US010973955B2

(12) United States Patent
Stefater, III et al.

(10) Patent No.: US 10,973,955 B2
(45) Date of Patent: *Apr. 13, 2021

(54) METHODS AND POLYMER COMPOSITIONS FOR TREATING RETINAL DETACHMENT AND OTHER OCULAR DISORDERS

(71) Applicant: Massachusetts Eye and Ear Infirmary, Boston, MA (US)

(72) Inventors: James Anthony Stefater, III, Boston, MA (US); Tomasz Pawel Stryjewski, Boston, MA (US)

(73) Assignee: MASSACHUSETTS EYE AND EAR INFIRMARY, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/952,214

(22) Filed: Nov. 19, 2020

(65) Prior Publication Data

US 2021/0077664 A1 Mar. 18, 2021

Related U.S. Application Data

(63) Continuation of application No. 16/245,397, filed on Jan. 11, 2019, now Pat. No. 10,874,767, which is a continuation of application No. PCT/US2017/041947, filed on Jul. 13, 2017.

(60) Provisional application No. 62/361,746, filed on Jul. 13, 2016.

(51) Int. Cl.
*A61L 27/52* (2006.01)
*A61L 27/26* (2006.01)
*A61L 27/58* (2006.01)

(52) U.S. Cl.
CPC .............. *A61L 27/52* (2013.01); *A61L 27/26* (2013.01); *A61L 27/58* (2013.01); *A61L 2400/06* (2013.01); *A61L 2430/16* (2013.01)

(58) Field of Classification Search
CPC .......... A61L 27/26; A61L 27/52; A61L 27/58; A61L 2400/06; A61L 2430/16
See application file for complete search history.

(56) References Cited

U.S. PATENT DOCUMENTS

| 5,654,349 A | 8/1997 | Feingold et al. |
| 7,833,206 B1 | 11/2010 | Lumpkin et al. |
| 9,072,809 B2 | 7/2015 | Askari et al. |
| 9,125,807 B2 | 9/2015 | Sawhney et al. |
| 9,623,144 B2 | 4/2017 | Askari et al. |
| 9,873,769 B2 | 1/2018 | Braithwaite et al. |
| 2006/0141049 A1 | 6/2006 | Lyons et al. |
| 2006/0292190 A1* | 12/2006 | Matier .................. A61K 9/0048 424/400 |
| 2009/0017097 A1 | 1/2009 | Sawhney et al. |
| 2012/0082730 A1 | 4/2012 | Banerjee et al. |
| 2014/0248231 A1 | 9/2014 | Askari et al. |
| 2015/0273108 A1 | 10/2015 | Askari et al. |
| 2016/0009872 A1* | 1/2016 | Braithwaite ............ A61L 26/00 424/78.27 |
| 2017/0175791 A1 | 6/2017 | Baur et al. |
| 2019/0175791 A1 | 6/2019 | Stefater, III et al. |
| 2019/0216982 A1 | 7/2019 | Roth et al. |
| 2019/0224375 A1 | 7/2019 | Stefater, III et al. |
| 2020/0338233 A1 | 10/2020 | Roth et al. |

FOREIGN PATENT DOCUMENTS

| CN | 101934089 A | 1/2011 |
| CN | 111741776 | 10/2020 |
| WO | WO-2013170195 A1 | 11/2013 |
| WO | WO-2016049791 A1 | 4/2016 |
| WO | WO-2018/013819 A1 | 1/2018 |
| WO | WO-2019/140184 A1 | 7/2019 |
| WO | WO-2019/140212 A1 | 7/2019 |

OTHER PUBLICATIONS

"Two Deans' Challenges garner 90 proposals", Harvard Gazette, https://news.harvard.edu/gazette/story/2016/03/two-deans-challenges-garner-90-proposals/, Mar. 9, 2016, accessed Jan. 8, 2019 (6 pages).
Alarake, N.Z. et al., "Mechanical properties and biocompatibility of in situ enzymatically cross-linked gelatin hydrogels", Int. J Artif Organs, 40(4):159-168. published online Mar. 18, 2017 (10 pages).
Almany, L. et al., "Biosynthetic hydrogel scaffolds made from fibrinogen and polyethylene glycol for 3D cell cultures", Biomaterials, 26:2467-2477, May 2005, available online Aug. 20, 2004 (11 pages).
Artzi, N. et al., "Characterization of Star Adhesive Sealants Based on PEG/Dextran Hydrogels", Macromol Biosci, 9:754-765, 2009 (12 pages).
Bai, X. et al., Dual crosslinked chondroitin sulfate injectable hydrogel formed via continuous Diels-Alder (DA) click chemistry for bone repair, Carbohydrate Polymers, 166:123-130, available online Feb. 20, 2017 (8 pages).
Baino, F., "The Use of Polymers in the Treatment of Retinal Detachment: Current Trends and Future Perspectives", Polymers, 2:286-322, Sep. 9, 2010 (37 pages).

(Continued)

*Primary Examiner* — Ali Soroush

(74) *Attorney, Agent, or Firm* — Wilmer Cutler Pickering Hale and Dorr LLP

(57) ABSTRACT

The invention provides methods and polymer compositions for treating retinal detachment and other ocular disorders, where the methods employ polymer compositions that can form a hydrogel in the eye of a subject. The hydrogel is formed by reaction of (i) a nucleo-functional polymer that is a biocompatible polymer containing a plurality of thio-functional groups —$R^1$—SH wherein $R^1$ is an ester-containing linker, such as a thiolated poly(vinyl alcohol) polymer and (ii) an electro-functional polymer that is a biocompatible polymer containing at least one thiol-reactive group, such as a poly(ethylene glycol) polymer containing alpha-beta unsaturated ester groups.

16 Claims, 8 Drawing Sheets

(56) References Cited

OTHER PUBLICATIONS

Bang, S. et al., "Injectable pullulan hydrogel for the prevention of postoperative tissue adhesion", International Journal of Biological Macromolecules, 87:155-162, Jun. 2016, published online Feb. 12, 2016 (8 pages).

Barth, H. et al., "A cross-linked hyaluronic acid hydrogel (Healaflow®) as a novel vitreous substitute", Graefes Arch Clin Exp Ophthalmol 254(4):697-703, published online Jan. 8, 2016 (7 pages).

Barth, H. et al., "A new model for in vitro testing of vitreous substitute candidates", Graefes Arch Clin Exp Ophthalmol 252:1581-1592, published online Jul. 25, 2014 (12 pages).

Bernkop-Schnürch, A., "Thiomers: A new generation of mucoadhesive polymers", Advanced Drug Delivery Reviews, 57:1569-1582, available online Sep. 19, 2005 (14 pages).

Boyd, S. et al., Management of Complications in Ophthalmic Surgery, Boyd and Wu, Eds., Jaypee-Highlights Medical Publishers, Inc., Panama, pp. 85-87, 2009 (5 pages).

Chang, J. et al., "An in situ-forming zwitterionic hydrogel as vitreous substitute", J. Mater. Chem. B, 3:1097-1105 (2015), first published Dec. 4, 2014 (9 pages).

Chang, S. et al., "Giant Retinal Tears—Surgical Techniques and Results Using Perfluorocarbon Liquids", Arch Ophthalmology, 107:761-766, May 1989, accessed Jan. 8, 2019 (6 pages).

Chen, X. et al., "Chitosan-based thermosensitive hydrogel as a promising ocular drug delivery system: Preparation, characterization, and in vivo evaluation", Journal of Biomaterials Applications, 27(4):391-402, 2011 (12 pages).

Chien, H-W. et al., "An in situ poly(carboxybetaine) hydrogel for tissue engineering applications", Biomater Sci, 5:322-330, published online Jan. 4, 2017 (9 pages).

Chien, Y. et al., "Corneal repair by human corneal keratocyte-reprogrammed iPSCs and amphiphatic carboxymethyl-hexanoyl chitosan hydrogel", Biomaterials, 33:8003-8016, available online Jul. 31, 2012 (14 pages).

Chirila, T.V. et al., "Synthetic Polymers as Materials for Artificial Vitreous Body: Review and Recent Advances", Journal of Biomaterials Applications, 9(2):121-37, Oct. 1994 (17 pages).

Chirila, T.V. et al., "The Use of Hydrophilic Polymers As Artificial Vitreous", Prog. Polym. Sci., 23:475-508, 1998 (34 pages).

Cho, E. et al., "Formulation and characterization of poloxamine-based hydrogels as tissue sealants", Acta Biomaterialia, 8(6):2223-2232, Mar. 8, 2012 (10 pages).

Cho, S-H. et al., "An injectable collagen/poly(γ-glutamic acid) hydrogel as a scaffold of stem cells and α-lipoic acid for enhanced protection against renal dysfunction", Biomater Sci., 5:285-294, 2017, published online Dec. 15, 2016 (10 pages).

Coseal® Surgical Sealant, Instructions for Use, Baxter Healthcare Corporation, Hayward, California, http://www.coseal.com/us/pdf/COSEAL_IFU.pdf, dated Mar. 2009 (2 pages).

Crafoord, S. et al., "Experimental vitreous tamponade using polyalkylimide hydrogel", Graefes Arch Clin Ophthalmol, 249(8):1167-1174, published online Mar. 31, 2011 (8 pages).

D'Souza, A. et al., "Polyethylene glycol (PEG): a versatile polymer for pharmaceutical applications", Expert Opinion on Drug Delivery, 13(9):1257-1275, Published online May 17, 2016 (20 pages).

Daniele, S. et al., "Glyceryl Methacrylate Hydrogel as a Vitreous Implant: An Experimental Study", Arch of Ophthal, 80(1):120-127, Jul. 1968, accessed Jan. 8, 2019 (7 pages).

Davidorf, F.H. et al., "Ocular Toxicity of Vitreal Pluronic Polyol F-127", Retina, 10(4):297-300, 1990 (4 pages).

De Jong, et al., "ADCON®-L Hydrogel as a Vitreous Substitute: Preliminary Results", Bulletin de la Société Belge Ophtalmologie, 278:71-75, 2000 (5 pages).

Deerenberg, E.B. et al., "Polyvinyl Alcohol Hydrogel Decreases Formation of Adhesions in a Rat Model of Peritonitis", Surgical Infections, 13(5):321-325, 2012 (5 pages).

Donati, S. et al., "Vitreous Substitutes: The Present and the Future", BioMed Research International, vol. 2014, Article 351804, pp. 1-12, May 4, 2014 (13 pages).

Dong, D. et al., "In Situ "Clickable" Zwitterionic Starch-Based Hydrogel for 3D Cell Encapsulation", ACS Applied Materials & Interfaces, 8:4442-4455, Jan. 28, 2016 (14 pages).

Dong, Y. et al., "Performance of an in situ formed bioactive hydrogel dressing from a PEG-based hyperbranched multifunctional copolymer", Acta Biomaterialia, 10:2076-2085, May 2014, available online Dec. 31, 2013 (10 pages).

Du, H. et al., "Injectable in situ Physically and Chemically Crosslinkable Gellan Hydrogel", Macromol Biosci., 12(7):952-961, Jul. 2012—Author Manuscript (24 pages).

Duker, J., "Chapter 6.30: Macular Hole", Ophthalmology, Third Edition, Yanoff, et al., Eds., Mosby Elsevier, pp. 682-685, 2009 (6 pages).

DuraSeal Product Information, Integra LifeSciences Corporation, Plainsboro, New Jersey, www.integralife.com, dated Jun. 2014 (2 pages).

Emoto, S. et al., "Intraperitoneal administration of cisplatin via an in situ cross-linkable hyaluronic acid-based hydrogel for peritoneal dissemination of gastric cancer", Surg Today, 44(5):919-926, 2014, published online Jul. 26, 2013 (8 pages).

Engelbert, M. et al., "Chapter 6.6, Vitrectomy", Ophthalmology, Third Edition, Yanoff, et al., Eds., Mosby Elsevier, pp. 530-533, 2009 (6 pages).

European Supplemental Search Report issued in EP17828468.3 dated Feb. 18, 2020 (8 pages).

Falabella, C.A. et al., "Novel Macromolecular Crosslinking Hydrogel to Reduce Intra-Abdominal Adhesions", Journal of Surgical Research, 159(2):772-778, Apr. 2010 (7 pages).

Fathalla, Z. M.A. et al., "Poloxamer-based thermoresponsive ketorolac tromethamine in situ gel preparations: Design, characterisation, toxicity and transcorneal permeation studies", Eur J. Pharm Biopharm, 114:119-134, published online Jan. 24, 2017 (16 pages).

FDA, Medical Devices Databases, Product Classification, Device: Fluid, Intraocular, Mar. 31, 2016, Advisory Committee/Planel Meetings—CDRH, last updated Jan. 1, 2019 (2 pages).

Fernández-Ferreiro, A. et al., "In vitro and in vivo ocular safety and eye surface permanence determination by direct and Magnetic Resonance Imaging of ion-sensitive hydrogels based on gellan gum and kappa-carrageenan", Eur J. Pharm Biopharm, 94:342-351, published online Jun. 14, 2015 (10 pages).

Foster, W.J. et al., "Internal Osmotic Pressure as a Mechanism of Retinal Attachment in a Vitreous Substitute", Journal of Bioactive and Compatible Polymers, 21:221-235, May 1, 2006 (15 pages).

Gao, Y. et al., "PLGA-PEG-PLGA hydrogel for ocular drug delivery of dexamethasone acetate", Drug Dev Ind Pharm, 36(10):1131-1138, 2010 (9 pages).

Ghobril, C. et al., "A Dendritic Thioester Hydrogel Based on Thiol-Thioester Exchange as a Dissolvable Sealant System for Wound Closure", Angew. Chem. Int. Ed, 52:14070-14074, 2013 (5 pages).

Ghosh, S. et al., "Strong poly(ethylene oxide) based gel adhesives via oxime cross-linking", Acta Biomaterialia, 29:206-214, Jan. 1, 2016, published online Oct. 22, 2015 (9 pages).

Gupta, H. et al., "Physiologically active hydrogel (in situ gel) of sparfloxacin and its evaluation for ocular retention using gamma scintigraphy", J Pharm Bioallied Sci., 7(3):195-200, Jul.-Sep. 2015 (8 pages).

Hassan, W. et al., "Encapsulation and 3D culture of human adipose-derived stem cells in an in-situ crosslinked hybrid hydrogel composed of PEG-based hyperbranched copolymer and hyaluronic acid", Stem Cell Research & Therapy, 4(2):32, Mar. 21, 2013 (11 pages).

HealaFlow, Product Information, Aptissen S.A., Geneva, Switzerland, http://www.aptissen.com/wp-content/uploads/2016/02/healaflow_brochure.pdf, accessed Jan. 29, 2019 (12 pages).

Hermann, C.D. et al., "Rapidly polymerizing injectable click hydrogel therapy to delay bone growth in a murine re-synostosis model", Biomaterials, 35(36):9698-9708, Dec. 2014, available online Aug. 28, 2014 (11 pages).

Hogen-Esch, T.E. et al., "Development of Injectable Poly(glyceryl Methacrylate) Hydrogels for Vitreous Prosthesis" Journal of Biomedical Materials Research, 10(6):975-976, 1976 (2 pages).

(56) References Cited

OTHER PUBLICATIONS

Hong, J.H. et al., "Injectable Polypeptide Thermogel as a Tissue Engineering System for Hepatogenic Differentiation of Tonsil-Derived Mesenchymal Stem Cells", Applied Materials & Interfaces, 9:11568-11576, Mar. 14, 2017 (9 pages).
Hong, Y. et al., "Biodegradation in vitro and retention in the rabbit eye of crosslinked poly(1-vinyl-2-pyrrolidinone) hydrogel as a vitreous substitute", Journal of Biomedical Materials Research, 39(4):650-659, 1998 (10 pages).
Hoshi, S. et al., "In Vivo and In Vitro Feasibility Studies of Intraocular Use of Polyethylene Glycol-Based Synthetic Sealant to Close Retinal Breaks in Porcine and Rabbit Eyes", Invest Ophthalmol Vis Sci, 56(8):4705-4711, Jul. 2015 (7 pages).
Hoshi, S. et al., "Polyethylene Glycol-Based Synthetic Hydrogel Sealant for Closing Vitrectomy Wounds: An In Vivo and Histological Study", Transl Vis Sci Technol, 5(3):Article 7, May 2016 (8 pages).
Huang, W. et al., "Preparation, pharmacokinetics and pharmacodynamics of ophthalmic thermosensitive in situ hydrogel of betaxolol hydrochloride", Biomed Pharmaco, 83:107-113, Oct. 2016 (7 pages).
Huynh, C.T. et al., "Synthesis, Characteristics and Potential Application of Poly(β-Amino Ester Urethane)-Based Multiblock Co-Polymers as an Injectable, Biodegradable and pH/Temperature-Sensitive Hydrogel System", Journal of Biomaterials Science 23:1091-1106, 2012 (17 pages).
International Search Report and Written Opinion as issued by U.S. Patent and Trademark Office as International Search Authority, in International Application PCT/US19/13223, dated Apr. 12, 2019 (9 pages).
International Search Report and Written Opinion issued by the Australian Patent Office in International Application No. PCT/US17/41947 dated Aug. 21, 2017 (8 pages).
International Search Report and Written Opinion issued by the U.S. Patent and Trademark Office as International Searching Authority, issued in PCT/US19/13185, dated Apr. 15, 2019 (9 pages).
Ishiyama, N. et al., "The prevention of peritendinous adhesions by a phospholipid polymer hydrogel formed in situ by spontaneous intermolecular interactions", Biomaterials, 31(14):4009-4016, May 2010, published online Feb. 10, 2010 (8 pages).
Kang, W. et al., "Photocrosslinked methacrylated carboxymethyl chitin hydrogels with tunable degradation and mechanical behavior", Carbohydrate Polymers, 160:18-25, 2017, published online Dec. 19, 2016 (8 pages).
Katagiri, Y. et al., "Application of Thermo-setting Gel as Artificial Vitreous", Japanese Journal of Ophthalmology, 49(6):491-96, 2005 (6 pages).
Kim, et al., "Dual Enzyme-Triggered In Situ Crosslinkable Gelatin Hydrogels for Artificial Cellular Microenvironments", Macromol Biosci, 16(11):1570-1576, 2016 (7 pages).
Kim, K.D. et al., "Polyethylene Glycol Hydrogel Spinal Sealant (DuraSeal Spinal Sealant) as an Adjunct to Sutured Dural Repair in the Spine: Results of a Prospective, Multicenter, Randomized Controlled Study", Spine, 36(23):1906-1912, Nov. 1, 2011 (7 pages).
Kleinberg, T.T. et al., "Vitreous Substitutes: A Comprehensive Review", Survey of Ophthalmology, 56(4):300-323, Jul.-Aug. 2011 (24 pages).
Kumar, D. et al., "Three-dimensional hypoxic culture of human mesenchymal stem cells encapsulated in a photocurable, biodegradable polymer hydrogel: A potential injectable cellular product for nucleus pulposus regeneration", Acta Biomater, 10:3463-3474, published online May 2, 2014 (12 pages).
Kwon, J.W. et al., "Biocompatibility of poloxamer hydrogel as an injectable intraocular lens: A pilot study", J Cataract Refract Surg, 31:607-613, 2005 (7 pages).
Lee H. et al., "Fast in situ enzymatic gelation of PPO-PEO block copolymer for injectable intraocular lens in vivo", J Biomater Appl, 28(8):1247-1263, 2014 (17 pages).
Li, C. et al., "Enhancement in bioavailability of ketorolac tromethamine via intranasal in situ hydrogel based on poloxamer 407 and carrageenan", Int J Pharm, 474(1-2):123-133, published online Aug. 17, 2014 (11 pages).
Li, et al. "Engineering in Situ Cross-Linkable and Neurocompatible Hydrogels", J Neurotrauma, 311431-1438, Aug. 15, 2014 (8 pages).
Li, L. et al., "Biodegradable and injectable in situ cross-linking chitosan-hyaluronic acid based hydrogels for postoperative adhesion prevention", Biomaterials, 35(12):3903-3917, available online Feb. 4, 2014 (15 pages).
Li, L. et al., "Injectable and Biodegradable pH-Responsive Hydrogels for Localized and Sustained Treatment of Human Fibrosarcoma", Applied Materials & Interfaces, 7:8033-8040, Apr. 2, 2015 (8 pages).
Li, Q. et al., "Biodegradable and photocrosslinkable polyphosphoester hydrogel", Biomaterials, 27:1027-1034, Mar. 2006, available online Aug. 24, 2005 (8 pages).
Li, S. et al., "Injectable PAMAM/ODex double-crosslinked hydrogels with high mechanical strength", Biomed. Mater, 12:015012, 2017, published online Dec. 9, 2016 (12 pages).
Li, X. et al., "A covalently crosslinked polysaccharide hydrogel for potential applications in drug delivery and tissue engineering", J Mater Sci: Mater Med, 23:2857-2865, published online Oct. 4, 2012 (9 pages).
Li, X. et al., "In situ gel-forming AP-57 peptide delivery system for cutaneous wound healing", Int J Pharm, 495(1):560-571, available online Sep. 9, 2015 (12 pages).
Liang, Y. et al., "An in situ formed biodegradable hydrogel for reconstruction of the corneal endothelium", Colloids Surf B: Biointerfaces, 82(1):1-7, 2011, available online Jul. 30, 2010 (7 pages).
Lin, C.-Y. et al., "In situ forming hydrogel composed of hyaluronate and polygalacturonic acid for prevention of peridural fibrosis", J Mater Sci: Mater Med, 26:168, published online Mar. 20, 2015 (12 pages).
Linh, N.T.B. et al., "Enzymatic in situ formed hydrogel from gelatin-tyramine and chitosan-4-hydroxylphenyl acetamide for the co-delivery of human adipose-derived stem cells and platelet-derived growth factor towards vascularization", Biomed. Mater., 12:015026, Feb. 24, 2017 (12 pages).
Liu, H. et al., "Thermosensitive injectable in-situ forming carboxymethyl chitin hydrogel for three-dimensional cell culture", Acta Biomaterialia, 35:228-237, published online Feb. 18, 2016 (10 pages).
Luo, Z. et al., "Thermosensitive PEG-PCL-PEG (PECE) hydrogel as an in situ gelling system for ocular drug delivery of diclofenac sodium", Drug Delivery, 23(1):63-68, 2016, published online Apr. 24, 2014 (7 pages).
Lv, Z., et al., "Thermosensitive in situ hydrogel based on the hybrid of hyaluronic acid and modified PCL/PEG triblock copolymer", Carbohydrate Polymers, 108:26-33, published online Mar. 21, 2014 (8 pages).
Mah, F.S. "Effect on Gel Formation Time of Adding Topical Ophthalmic Medications to ReSure Sealant, an In Situ Hydrogel", J Ocul Pharmacol Ther, 32(6):396-399, 2016 (5 pages).
Maruoka, S. et al., "Biocompatibility of Polyvinylalcohol Gel as a Vitreous Substitute", Current Eye Research, 31(7-8):599-606, 2006 (9 pages).
Masket, S. et al., "Hydrogel sealant versus sutures to prevent fluid egress after cataract surgery", J Cataract Refract Surg, 40:2057-2066, 2014 (10 pages).
Mazza, E. et al., "Mechanical biocompatibility of highly deformable biomedical materials", J Mech Behav Biomed Mater, 48:100-124, available online Apr. 1, 2015 (25 pages).
McKay, C.A. et al., "An Injectable, Calcium Responsive Composite Hydrogel for the Treatment of Acute Spinal Cord Injury", ACS Applied Materials & Interfaces, 6(3):1424-1438, Jan. 3, 2014 (15 pages).
Migliavacca, et al., "Experimental short-term tolerance to perfluorodecalin in the rabbit eye: a histopathologic study", Current Eye Research, 17(8):828-835, 1998 (9 pages).
Miki, D.et al., "A Photopolymerized Sealant for Corneal Lacerations", Cornea, 21(4):393-399, May 2002 (7 pages).

(56) References Cited

OTHER PUBLICATIONS

Miles, D.E. et al., "Peptide: glycosaminoglycan hybrid hydrogels as an injectable intervention for spinal disc degeneration", J Materials Chemistry B, Materials for Biology and Medicine, 4(19):3225-3231, May 11, 2016 (8 pages).
Morelli, A. et al., "Design, preparation and characterization of ulvan based thermosensitive hydrogels", Carbohydrate Polymers, 136:1108-1117, 2016, available online Oct. 13, 2015 (10 pages).
Na, S.Y. et al., "Hyaluronic acid/mildly crosslinked alginate hydrogel as an injectable tissue adhesion barrier", J Mater Sci: Mater Med, 23:2303-2313, published online Jun. 3, 2012 (11 pages).
Naderi-Meshkin, H. et al., "Chitosan-based injectable hydrogel as a promising in situ forming scaffold for cartilage tissue engineering", Cell Biol Int, 38(1):72-84, Jan. 2014, published online Oct. 15, 2013 (14 pages).
Nam, K. et al,. "Modeling of swelling and drug release behavior of spontaneously forming hydrogels composed of phospholipid polymers", Int J. Pharm, 275(1-2):259-269, May 2004 (11 pages).
Nam, K. et al., "pH-modulated release of insulin entrapped in a spontaneously formed hydrogel system composed of two water-soluble phospholipid polymers", J Biomater. Sci. Polym Edn., 13(11):1259-1269, 2002 (12 pages).
Nie, W. et al., "Rapidly in situ forming chitosan/c-polylysine hydrogels for adhesive sealants and hemostatic materials", Carbohydrate Polymers, 96:342-348, available online Apr. 15, 2013 (7 pages).
Ossipov, D.A. et al., "Poly(vinyl alcohol) Cross-Linkers for in Vivo Injectable Hydrogels", Macromolecules, 41(11):3971-3982, 2008, accessed Jan. 8, 2019 (12 pages).
Parel, J-M. et al., "Chapter 129: Silicone Oils: Physicochemical Properties", Retina: vol. I, Fourth Edition, Ryan, Editor, Mosby Elsevier, pp. 2191-2210, 2006 (22 pages).
Patel, S.P. et al., "Novel Thermosensitive Pentablock Copolymers for Sustained Delivery of Proteins in the Treatment of Posterior Segment Diseases", Protein Pept Lett, 21(11):1185-1200, 2014—Author Manuscript (34 pages).
Peyman, G.A. et al., "Diagnostic and Surgical Techniques: Perfluorocarbon Liquids in Ophthalmology", Kramer, et al., eds., Survey of Ophthalmology, 39(5):375-395, 1995 (21 pages).
Quinteros, D.A. et al., "Evaluation of the Performance of an Ophthalmic Thermosensitive Hydrogel Containing Combination of Suramin and Bevacizumab", Current Pharmaceutical Design, 22:1-9, 2016 (9 pages).
Ramakumar, S. et al., "Local Hemostasis during Laparoscopic Partial Nephrectomy Using Biodegradable Hydrogels: Initial Porcine Results", Journal of Endourology, 16(7):489-494, Sep. 2002 (6 pages).
ReSure® Sealant Product Information, Instructions for Use, Ocular Therapeutix, Bedford, Massachusetts, https://www.resuresealant.com/wp-content/uploads/2017/05/LCN-80/1004-011-Rev-C-ReSure-Sealant-Instructions-for-Use.pdf, accessed Jan. 29, 2019 (2 pages).
Sakai, S. et al., "Peritoneal adhesion prevention by a biodegradable hyaluronic acid-based hydrogel formed in situ through a cascade enzyme reaction initiated by contact with body fluid on tissue surfaces", Acta Biomaterialia, 24:152-158, Sep. 2015 (7 pages).
Sanders, L. et al., "Mechanical Characterization of a Bi-functional Tetronic Hydrogel Adhesive for Soft Tissues", J Biomed Mater Res A., 103(3):861-868, Mar. 2015—Author Manuscript (19 pages).
Santhanam, S. et al., "Biomimetic hydrogel with tunable mechanical properties for vitreous substitutes", Acta Biomaterialia, 43:327-337, published online Jul. 29, 2016 (11 pages).
Shazly, T.M. et al., "Augmentation of postswelling surgical sealant potential of adhesive hydrogels", Journal of Biomedical Materials Research A, 95A(4):1159-1169, published online Sep. 28, 2010 (11 pages).
Steffensen, S.L. et al., "Soft hydrogels interpenetrating silicone—A polymer network for drug-releasing medical devices", J Biomed Mater Res Part B, 104B:402-410, 2016, published online Apr. 17, 2015 (9 pages).
Svirkin, Y. et al., "Biodegradable thiol-modified poly(vinyl alcohol) hydrogels", Materials Research Society, MRS 2013, Cambridge Polymer Group, Presentation 7-17, Oct. 1, 2010 (14 pages).
Swindle, K. et al., "Recent advances in polymeric vitreous substitutes", Expert Review of Ophthalmology, 2(2):255-265, 2007 (11 pages).
Swindle-Reilly, K.E. et al., "Chapter 13: Designing hydrogels as vitreous substitutes in ophthalmic surgery", Biomaterials and Regenerative Medicine in Ophthalmology, Traian Chirila, Ed., Woodhead Publishing, Sawston, Cambridge, Great Britain, pp. 339-373, 2010 (36 pages).
Swindle-Reilly, K.E. et al., "Rabbit Study of an In Situ Forming Hydrogel Vitreous Substitute", Investigative Ophthalmology & Visual Science, 50(10):4840-4846, Oct. 2009 (7 pages).
Taich, P. et al., "Sustained-release hydrogels of topotecan for retinoblastoma", Colloids and Surfaces B: Biointerfaces, 146:624-631, published online Jul. 2, 2016 (8 pages).
Takahashi, A. et al., "In Situ Cross-Linkable Hydrogel of Hyaluronan Produced via Copper-Free Click Chemistry", Biomacromolecules, 14:3581-3588, Sep. 4, 2013 (8 pages).
Tan, J. et al., "Improved cell adhesion and proliferation on synthetic phosphonic acid-containing hydrogels", Biomaterials, 26:3663-3671, Jun. 2005 (9 pages).
Tao, Y. et al., "Evaluation of an in situ chemically crosslinked hydrogel as a long-term vitreous substitute material", Acta Biomaterialia, 9:5022-5030, Feb. 2013, available online Sep. 27, 2012 (9 pages).
Tortora, M. et al., "Michael-Type Addition Reactions for the In Situ Formation of Poly(vinyl alcohol)-Based Hydrogels", Biomacromolecules, 7(1):209-214, 2007 (6 pages).
Transparency Market Research, "Vitreous Tamponades Market: (By Types: Gases, Silicone Oil and Perfluorocarbons)—Global Industry Analysis, Size, Growth, Trends and Forecast, 2014-2020", 2015 (73 pages).
Vaziri, K. et al., "Tamponade in the surgical management of retinal detachment", Clinical Ophthalmology, 10:471-476, 2016 (6 pages).
Vijayasekaran, S. et al., "Poly(1-Vinyl-2-Pyrrolidinone) Hydrogels as Vitreous Substitutes: Histopathological Evaluation in the Animal Eye", Journal of Biomaterials Science, Polymer Edition, 7(8):685-696, 1996 (13 pages).
Villa-Camacho, J.C. et al., "The efficacy of a lysine-based dendritic hydrogel does not differ from those of commercially available tissue sealants and adhesives: an ex vivo study", BMC Musculoskeletal Disorders, 16:116, May 2015 (6 pages).
Vulpe, R. et al., "Rheological study of in-situ crosslinkable hydrogels based on hyaluronanic acid, collagen and sericin", Materials Science and Engineering C, 69:388-397, published online Jul. 5, 2016 (10 pages).
Wallace, D.G. et al., "A Tissue Sealant Based on Reactive Multifunctional Polyethylene Glycol", J Biomed Mater Res (Appl Biomater), 58(5):545-555, 2001 (11 pages).
Wang, J. et al., "In Situ-Forming Polyamidoamine Dendrimer Hydrogels with Tunable Properties Prepared via Aza-Michael Addition Reaction", Applied Materials & Interfaces, 9:10494-10503, Mar. 6, 2017 (10 pages).
Wang, R. et al., "Fast in situ generated ε-polylysine-poly (ethylene glycol) hydrogels as tissue adhesives and hemostatic materials using an enzyme-catalyzed method", J Biomater Appl, 29(8):1167-1179, 2015 (13 pages).
Wang, T. et al., "Preparation and properties of a novel thermosensitive hydrogel based on chitosan/hydroxypropyl methylcellulose/glycerol", International Journal of Biological Macromolecules, 93:775-782, published online Sep. 14, 2016 (8 pages).
Wathier, M. et al., "Dendritic Macromers as in Situ Polymerizing Biomaterials for Securing Cataract Incisions", J Am Chem Soc, 126(40):12744-12745, published online Sep. 21, 2004 (9 pages).
Wei, C-Z. et al., "A thermosensitive chitosan-based hydrogel barrier for post-operative adhesions' prevention", Biomaterials, 30:5534-5540, published online Aug. 3, 2009 (7 pages).
Weng, L. et al., "An in situ forming biodegradable hydrogel-based embolic agent for interventional therapies", Acta Biomaterialia, 9:8182-8191, published online Jun. 19, 2013 (10 pages).

(56) References Cited

OTHER PUBLICATIONS

Xu, Y. et al., "Spontaneous Packaging and Hypothermic Storage of Mammalian Cells with a Cell-Membrane-Mimetic Polymer Hydrogel in a Microchip", Applied Materials & Interfaces, 7:23089-23097, Oct. 5, 2015 (9 pages).

Xu, Y. et al., "Synthesis, characterization, biodegradability and biocompatibility of a temperature-sensitive PBLA-PEG-PBLA hydrogel as protein delivery system with low critical gelation concentration", Drug Development and Industrial Pharmacy, 40(9):1264-1275, 2014, published online Jul. 15, 2013 (13 pages).

Yin, H. et al., "Toxicity Evaluation of Biodegradable and Thermosensitive PEG-PCL-PEG Hydrogel as a Potential In Situ Sustained Ophthalmic Drug Delivery System", J Biomed Mater Res B: Appl Biomater, 92B(1):129-137, 2010, published online Oct. 2, 2009 (9 pages).

Yu, J. et al., "In situ covalently cross-linked PEG hydrogel for ocular drug delivery applications", International Journal of Pharmaceutics, 470(1-2):151-157, available online Apr. 23, 2014 (7 pages).

Yu, Y. et al., "Injectable Chemically Crosslinked Hydrogel for the Controlled Release of Bevacizumab in Vitreous: A 6-Month In Vivo Study", http://tvstjournal.org/doi/full/10.1167/tvst.4.2.5, translational vision science & technology, 4(2):Article 5, Mar. 2015 (11 pages).

Zarembinski, T.I. et al., "Thiolated hyaluronan-based hydrogels crosslinked using oxidized glutathione: An injectable matrix designed for ophthalmic applications", Acta Biomaterialia, 10:94-103, 2014, published online Oct. 1, 2013 (10 pages).

Zawaneh, P.N. et al., "Design of an injectable synthetic and biodegradable surgical biomaterial", PNAS, 107(24):11014-11019, Jun. 15, 2010 (6 pages).

Zhao, X. et al., "Photocrosslinkable Gelatin Hydrogel for Epidermal Tissue Engineering", Advanced Healthcare Materials, 5:108-118, 2016 (11 pages).

Zhou, Y. et al., "Rapid Gelling Chitosan/Polylysine Hydrogel with Enhanced Bulk Cohesive and Interfacial Adhesive Force: Mimicking Features of Epineurial Matrix for Peripheral Nerve Anastomosis", Biomacromolecules, 17(2):622-630, Jan. 18, 2016 (9 pages).

* cited by examiner

METHODS AND POLYMER COMPOSITIONS FOR TREATING RETINAL DETACHMENT AND OTHER OCULAR DISORDERS

CROSS REFERENCE TO RELATED APPLICATIONS

This application is a continuation of U.S. patent application Ser. No. 16/245,397, filed on Jan. 11, 2019, which is a continuation of International Application No. PCT/US2017/041947, filed on Jul. 13, 2017, which claims the benefit of and priority to U.S. Provisional Patent Application Ser. No. 62/361,746, filed Jul. 13, 2016, the disclosures of each of which are hereby incorporated by reference in their entireties.

FIELD OF THE INVENTION

The invention provides methods and polymer compositions for treating retinal detachment and other ocular disorders, where the methods employ polymer compositions that can form a hydrogel in the eye of a subject.

BACKGROUND

Disorders of the retina are a common cause of debilitating vision loss. Surgery can be required as part of a treatment regimen for various disorders of the retina, such as retinal detachments, retinal tears, and macular holes. The first step in such surgeries is removal of the vitreous gel that fills the eye (i.e., a vitrectomy), thereby permitting surgical access to the retinal tissue. At the end of these vitrectomies, an agent (i.e., a tamponade agent) is placed in the eye to apply force to the retina and desirably seal any retinal breaks, thereby keeping retinal tissue in its desired location while the retina heals. Tamponade agents commonly used in current medical practice include an expansive gas and silicone oil.

The currently available expansive gas and silicone oil tamponade agents have multiple features that are undesirable. For example, patients treated with an expansive gas tamponade agent must remain in a face-down position for several weeks after surgery, the patients' post-operative vision quality is typically poor, and patients are generally not permitted to travel by airplane or to high altitudes for several months. In addition, the expansive gas tamponade agent is often poorly effective in supporting retinal tissue in the bottom half of the retina, which poses a problem when the retinal pathology is located in the bottom half of the retina. A silicone oil tamponade agent suffers the disadvantages that it substantially distorts the patient's vision, the patient must undergo a second surgery to remove the silicone oil from the eye after the retinal tissue has healed, and oil applies a weaker tamponade force relative to gas.

The foregoing and other limitations of tamponade agents commonly used in current medical practice have prompted investigations into using other materials as a tamponade agent. Exemplary alternative materials investigated for use as tamponade agents include, for example, various polymer materials such as described in, for example, Baino in *Polymers* (2010) vol. 2, pages 286-322; Crafoord et al. in *Graefes Arch. Cln. Exp. Ophthalmol.* (2011) vol. 249, pages 1167-1174; and U.S. Pat. No. 9,072,809. However, it is difficult to achieve a polymer composition that can be easily administered to the eye, that once in eye provides sufficient support/pressure on the entire retina, is not toxic to the patient, is optically clear, and undergoes biodegradation at an appropriate rate so that the retinal tissue is supported for an appropriate amount of time to facilitate healing of retinal tissue following a vitrectomy without having to perform a second surgery to remove the tamponade agent.

Accordingly, the need exists for new retinal tamponade agents and methods for installing a retinal tamponade and/or treating retinal detachment and other ocular disorders. The present invention addresses this need and provides other related advantages.

SUMMARY

The invention provides methods and polymer compositions for treating retinal detachment and other ocular disorders, where the methods employ polymer compositions that can form a hydrogel in the eye of a subject. The methods involve administering to the eye of the subject (i) a nucleo-functional polymer that is a biocompatible polymer containing a plurality of thio-functional groups —$R^1$—SH wherein $R^1$ is an ester-containing linker, and (ii) an electrofunctional polymer that is a biocompatible polymer containing at least one thiol-reactive group, such as an alpha-beta unsaturated ester. The nucleo-functional polymer and electro-functional polymer are desirably low-viscosity materials that can be injected easily into the eye of a patient through a narrow-gauge needle, thereby permitting administration of the polymers through small surgical ports in the eye of the patient. This minimizes trauma to the patient's eye and is surgically feasible. The nucleo-functional polymer and electro-functional polymer begin to react spontaneously once mixed, where the vast majority of reaction between the nucleo-functional polymer and electro-functional polymer occurs while the polymers are in the patient's eye thereby forming a hydrogel in the eye of the patient that will apply pressure to and support retinal tissue in the eye of the patient.

One exemplary advantage of the methods and polymer compositions described herein is that no toxic initiator agent or ultra-violet light is required to facilitate reaction between the nucleo-functional polymer and electro-functional polymer. Additional exemplary advantages of methods and polymer compositions described herein is that reaction between the nucleo-functional polymer and electro-functional polymer does not generate byproducts or result in the formation of any medically significant heat. Thus, the methods and polymer compositions described herein are much safer than various polymer compositions described in literature previously. Still further exemplary advantages of the methods and polymer compositions described herein is that the polymers can be inserted through small surgical ports in the eye of the patient without causing any significant degradation of the polymer, and the resulting hydrogel formed by reaction of the polymers is non-toxic and undergoes biodegradation at a rate appropriate to support the retinal tissue over the timeframe necessary for healing of the retinal tissue. The appropriate biodegradation rate is advantageous because, for example, natural clearance of the hydrogel from the patient's eye at the appropriate time avoids having to perform a subsequent surgery to remove the hydrogel tamponade agent. Various aspects and embodiments of the invention are described in further detail below, along with further description of multiple advantages provided by the invention.

Accordingly, one aspect of the invention provides a method of contacting retinal tissue in the eye of a subject with a hydrogel. The method comprises (a) administering to the vitreous cavity of an eye of the subject an effective amount of a nucleo-functional polymer and an electrofunctional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —R¹—SH wherein R¹ is an ester-containing linker, and the electro-functional polymer is a biocompatible polymer containing at least one thiol-reactive group. The nucleo-functional polymer and the electro-functional polymer may be administered together as a single composition to the vitreous cavity of the eye of the subject, or alternatively the nucleo-functional polymer and the electro-functional polymer may be administered separately to the vitreous cavity of the eye of the subject. The method may be further characterized according, for example, the identity of the nucleo-functional polymer, electrofunctional polymer, and physical characteristics of the hydrogel formed therefrom, as described in the detailed description below. Exemplary subjects that may benefit from the method include, for example, subjects having a physical discontinuity in the retinal tissue, such as subjects having a tear in the retinal tissue, a break in the retinal tissue, or a hole in the retinal tissue. In certain embodiments, the subject has undergone surgery for a macular hole or has undergone a vitrectomy for vitreomacular traction. In certain other embodiments, the subject has undergone surgery to repair a serous retinal detachment, to repair a tractional retinal detachment, or to remove at least a portion of an epiretinal membrane.

Another aspect of the invention provides a method of supporting retinal tissue in the eye of a subject, the method comprising: (a) administering to the vitreous cavity of an eye of the subject an effective amount of a nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —R¹—SH wherein R¹ is an ester-containing linker, and the electro-functional polymer is a biocompatible polymer containing at least one thiol-reactive group. The nucleo-functional polymer and the electro-functional polymer may be administered together as a single composition to the vitreous cavity of the eye of the subject, or alternatively the nucleo-functional polymer and the electro-functional polymer may be administered separately to the vitreous cavity of the eye of the subject. The method may be further characterized according, for example, the identity of the nucleo-functional polymer, electro-functional polymer, and physical characteristics of the hydrogel formed therefrom, as described in the detailed description below. Exemplary subjects that may benefit from the method include, for example, subjects having a physical discontinuity in the retinal tissue, such as subjects having a tear in the retinal tissue, a break in the retinal tissue, or a hole in the retinal tissue. In certain embodiments, the subject has undergone surgery for a macular hole or has undergone a vitrectomy for vitreomacular traction. In certain other embodiments, the subject has undergone surgery to repair a serous retinal detachment, to repair a tractional retinal detachment, or to remove at least a portion of an epiretinal membrane.

Another aspect of the invention provides a method of treating a subject with a retinal detachment, the method comprising: (a) administering an effective amount of a nucleo-functional polymer and an electro-functional polymer to the vitreous cavity of an eye of the subject with a detachment of at least a portion of retinal tissue; and (b) allowing the nucleo-functional polymer and the electro-functional polymer to react to form a hydrogel in the vitreous cavity; wherein the hydrogel supports the retinal tissue during reattachment of the portion of the retinal tissue, the nucleo-functional polymer is a biocompatible polymer containing a plurality of thio-functional groups —R¹—SH wherein R¹ is an ester-containing linker, and the electro-functional polymer is a biocompatible polymer containing at least one thiol-reactive group. The nucleo-functional polymer and the electro-functional polymer may be administered together as a single composition to the vitreous cavity of the eye of the subject, or alternatively the nucleo-functional polymer and the electro-functional polymer may be administered separately to the vitreous cavity of the eye of the subject. The method may be further characterized according, for example, the identity of the nucleo-functional polymer, electro-functional polymer, and physical characteristics of the hydrogel formed therefrom, as described in the detailed description below. The retinal detachment may be, for example, a rhegmatogenous retinal detachment, a tractional retinal detachment, or a serous retinal detachment.

Another aspect of the invention provides an injectable, ocular formulation for forming a hydrogel in the eye of a subject, the formulation comprising: (a) a nucleo-functional polymer that is a biocompatible polymer containing a plurality of thio-functional groups —R¹—SH wherein R¹ is an ester-containing linker; (b) an electro-functional polymer that is a biocompatible polymer containing at least one thiol-reactive group; and (c) a liquid pharmaceutically acceptable carrier for administration to the eye of a subject. Such injectable, ocular formulation for forming a hydrogel may be used in the methods described herein.

The nucleo-functional polymer may be, for example, a biocompatible polymer selected from a polyalkylene and polyheteroalkylene polymer each being substituted by (i) a plurality of thio-functional groups —R¹—SH, and optionally (ii) one or more hydroxyl, alkyl ester, hydroxyalkyl ester, or amide groups. In certain embodiments, the nucleo-functional polymer is a biocompatible poly(vinyl alcohol) polymer comprising:

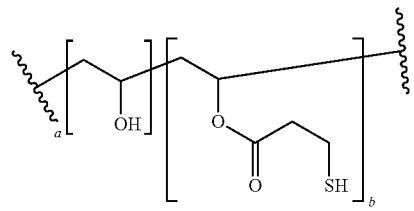

wherein a is an integer from 1-10 and b is an integer from 1-10.

The electro-functional polymer may be, for example, a biocompatible polymer selected from a polyalkylene and polyheteroalkylene polymer each being substituted by at least one thiolreactive group. In certain embodiments, the thiol-reactive group is —OC(O)CH=CH₂. In yet other embodiments, the electro-functional polymer has the formula:

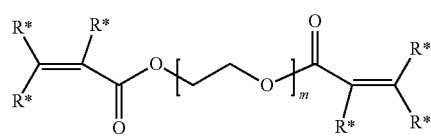

wherein R* is independently for each occurrence hydrogen, alkyl, aryl, or aralkyl; and m is an integer in the range of 5 to 15,000.

DETAILED DESCRIPTION OF THE INVENTION

Figure 1:
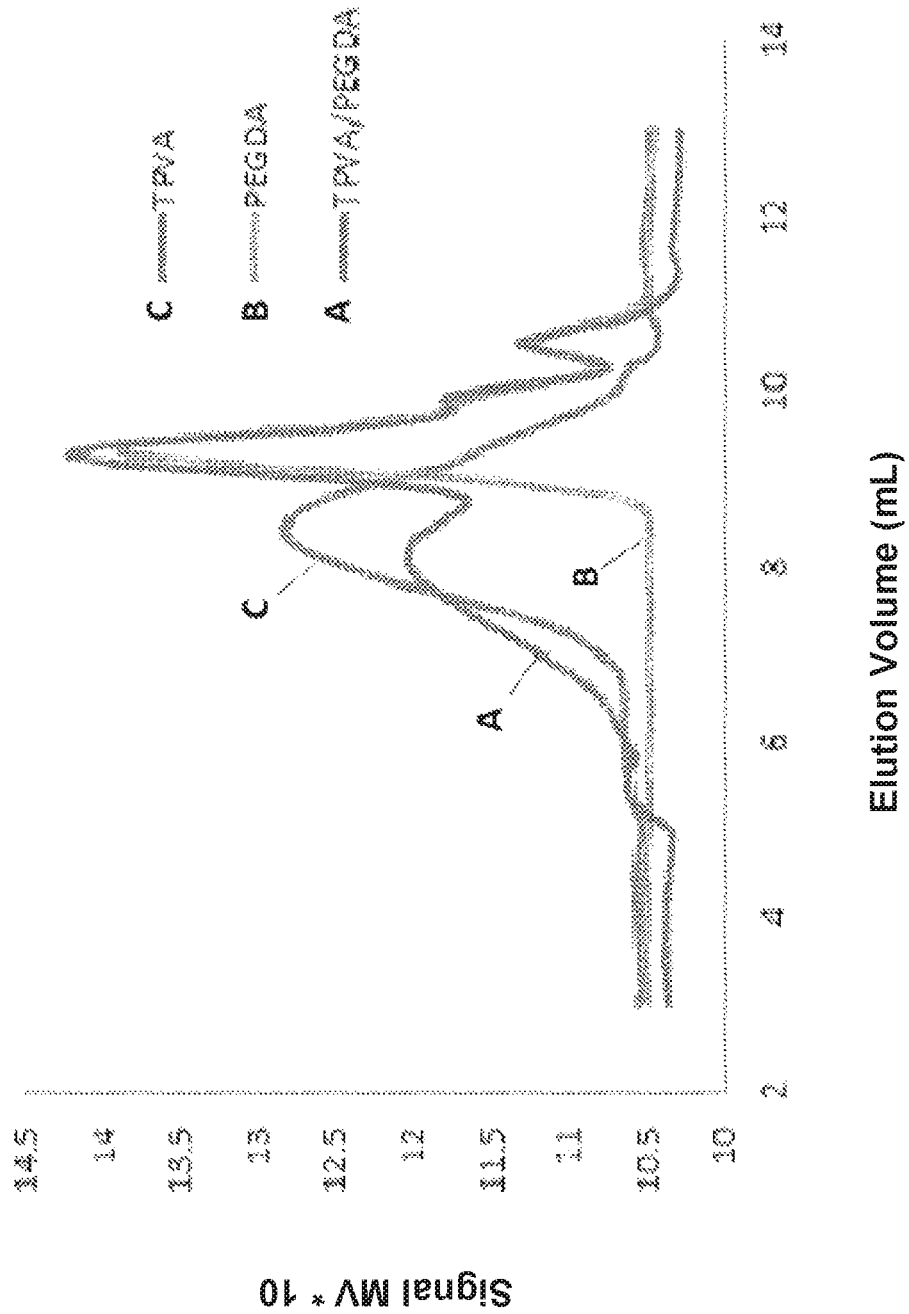
FIG. 1 is a GPC chromatograph showing exemplary starting materials (i.e., TPVA and PEGDA) and degradation products of a hydrogel subjected to degradation conditions, as further described in Example 1 where the hydrogel was formed by reaction of thiolated poly(vinyl alcohol) and poly(ethylene glycol)-diacrylate.

The invention provides methods and polymer compositions for treating retinal detachment and other ocular disorders, where the methods employ polymer compositions that can form a hydrogel in the eye of a subject. The methods involve administering to the eye of the subject (i) a nucleo-functional polymer that is a biocompatible polymer containing a plurality of thio-functional groups —$R^1$—SH wherein $R^1$ is an ester-containing linker, and (ii) an electrofunctional polymer that is a biocompatible polymer containing at least one thiol-reactive group, such as an alpha-beta unsaturated ester. The nucleo-functional polymer and electro-functional polymer are desirably low-viscosity materials that can be injected easily into the eye of a patient through a narrow-gauge needle, thereby permitting administration of the polymers through small surgical ports in the eye of the patient. This minimizes trauma to the patient's eye. The nucleofunctional polymer and electro-functional polymer begin to react spontaneously once mixed, where the vast majority of reaction between the nucleo-functional polymer and electro-functional polymer occurs while the polymers are in the patient's eye thereby forming a hydrogel in the eye of the patient that will apply pressure to and support retinal tissue in the eye of the patient.

One exemplary advantage of the methods and polymer compositions described herein is that no toxic initiator agent or ultra-violet light is required to facilitate reaction between the nucleofunctional polymer and electro-functional polymer. Additional exemplary advantages of methods and polymer compositions described herein is that reaction between the nucleo-functional polymer and electro-functional polymer does not generate byproducts or result in the formation of any medically significant heat. Thus, the methods and polymer compositions described herein are much safer than various polymer compositions described in literature previously. Still further exemplary advantages of the methods and polymer compositions described herein is that the polymers can be inserted through small surgical ports in the eye of the patient without causing any significant degradation of the polymer, and the resulting hydrogel formed by reaction of the polymers is nontoxic and undergoes biodegradation at a rate appropriate to support the retinal tissue over the time-frame necessary for healing of the retinal tissue. The appropriate biodegradation rate is advantageous because, for example, natural clearance of the hydrogel from the patient's eye at the appropriate time avoids having to perform a subsequent surgery to remove the hydrogel tamponade agent.

Various aspects of the invention are set forth below in sections; however, aspects of the invention described in one particular section are not to be limited to any particular section.

I. Definitions

To facilitate an understanding of the present invention, a number of terms and phrases are defined below.

The terms "a" and "an" as used herein mean "one or more" and include the plural unless the context is inappropriate.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is substituted at one or more ring positions with halogen, alkyl, hydroxyl, or alkoxyl. In certain other embodiments, the aromatic ring is not substituted, i.e., it is unsubstituted.

The term "aralkyl" refers to an alkyl group substituted with an aryl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted.

The term "heteroaralkyl" refers to an alkyl group substituted with a heteroaryl group.

The terms ortho, meta and para are art-recognized and refer to 1,2-, 1,3- and 1,4-disubstituted benzenes, respectively. For example, the names 1,2-dimethylbenzene and orthodimethylbenzene are synonymous.

The terms "heterocyclyl" and "heterocyclic group" are art-recognized and refer to saturated or partially unsaturated 3- to 10-membered ring structures, alternatively 3- to 7-membered rings, whose ring structures include one to four heteroatoms, such as nitrogen, oxygen, and sulfur. The number of ring atoms in the heterocyclyl group can be specified using $C_x$-$C_x$ nomenclature where x is an integer specifying the number of ring atoms. For example, a $C_3$-$C_7$heterocyclyl group refers to a saturated or partially unsaturated 3- to 7-membered ring structure containing one to four heteroatoms, such as nitrogen, oxygen, and sulfur. The designation "$C_3$-$C_7$" indicates that the heterocyclic ring contains a total of from 3 to 7 ring atoms, inclusive of any heteroatoms that occupy a ring atom position. One example of a $C_3$heterocyclyl is aziridinyl. Heterocycles may also be mono-, bi-, or other multi-cyclic ring systems. A heterocycle may be fused to one or more aryl, partially unsaturated, or saturated rings. Heterocyclyl groups include, for example, biotinyl, chromenyl, dihydrofuryl, dihydroindolyl, dihydropyranyl, dihydrothienyl, dithiazolyl, homopiperidinyl, imidazolidinyl, isoquinolyl, isothiazolidinyl, isoxazolidinyl, morpholinyl, oxolanyl, oxazolidinyl, phenoxanthenyl, piperazinyl, piperidinyl, pyranyl, pyrazolidinyl, pyrazolinyl, pyridyl, pyrimidinyl, pyrrolidinyl, pyrrolidin-2-onyl, pyrrolinyl, tetrahydrofuryl, tetrahydroisoquinolyl, tetrahydropyranyl, tetrahydroquinolyl, thiazolidinyl, thiolanyl, thiomorpholinyl, thiopyranyl, xanthenyl, lactones, lactams such as azetidinones and pyrrolidinones, sultams, sultones, and the like. Unless specified otherwise, the heterocyclic ring is optionally substituted at one or more positions with substituents such as alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. In certain embodiments, the heterocyclcyl group is not substituted, i.e., it is unsubstituted.

The terms "amine" and "amino" are art-recognized and refer to both unsubstituted and substituted amines, e.g., a moiety represented by the general formula —N($R^{50}$)($R^{51}$), wherein $R^{50}$ and $R^{51}$ each independently represent hydrogen, alkyl, cycloalkyl, heterocyclyl, alkenyl, aryl, aralkyl, or —(CH$_2$)$_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—$R_{61}$, where m and $R_{61}$ are described above.

The term "amide" or "amido" as used herein refers to a radical of the form —$R_a$C(O)N($R_b$)—, —$R_a$C(O)N($R_b$) $R_c$—, —C(O)N$R_b$$R_c$, or —C(O)NH$_2$, wherein $R_a$, $R_b$ and $R_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and Re may be joined to form a 3- to 12-membered ring, such as a 3- to 10-membered ring or a 5- to 6-membered ring.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise.

As used herein, the terms "subject" and "patient" refer to organisms to be treated by the methods of the present invention. Such organisms are preferably mammals (e.g., murines, simians, equines, bovines, porcines, canines, felines, and the like), and more preferably humans.

As used herein, the term "effective amount" refers to the amount of a compound (e.g., a compound of the present invention) sufficient to effect beneficial or desired results. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. In certain embodiments, the pharmaceutically acceptable carrier is, or comprises, balanced salt solution. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. [1975]. The compositions may optionally contain a dye. Accordingly, in certain embodiments, the composition further comprises a dye.

Throughout the description, the molecular weight of a polymer is weight-average molecular weight unless the context clearly indicates otherwise, such as clearly indicating that the molecular weight of the polymer is the number-average molecular weight.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

II. Therapeutic Methods and Injectable, Ocular Formulations for Forming A Hydrogel The invention provides methods and polymer compositions for treating retinal detachment and other ocular disorders, where the methods employ polymer compositions that can form a hydrogel in the eye of a subject. The methods include, for example, methods for contacting retinal tissue in the eye of a subject with a hydrogel, methods for supporting retinal tissue, methods for treating a subject with a retinal detachment, and methods for treating hypotony, methods for treating a choroidal effusion, methods for supporting tissue in or adjacent to the anterior chamber of the eye, and methods of maintaining or expanding a nasolacrimal duct, and injectable, ocular formulations for forming a hydrogel. The methods and compositions are described in more detail below.

First Method—Contacting Retinal Tissue in the Eye of a Subject with a Hydrogel

One aspect of the invention provides a method of contacting retinal tissue in the eye of a subject with a hydrogel. The method comprises (a) administering to the vitreous cavity of an eye of the subject an effective amount of a nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group.

The method can be further characterized by, for example, the identity of the subject. In certain embodiments, subject has a physical discontinuity in the retinal tissue. In certain embodiments, the physical discontinuity is a tear in the retinal tissue, a break in the retinal tissue, or a hole in the retinal tissue. In other embodiments, the subject has undergone surgery for a macular hole, has undergone surgery to remove at least a portion of a epiretinal membrane, or has undergone a vitrectomy for vitreomacular traction. In other embodiments, the subject has a detachment of at least a portion of the retinal tissue. The retinal detachment may be, for example, a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to produce a hydrogel that contacts retinal tissue. This effective amount may vary depending on the volume of the eye cavity to be filled, such that a large eye cavity will require more nucleo-functional polymer and an electro-functional polymer to produce a hydrogel occupying more volume, as can be readily determined by those of skill in the art based on the teachings provided herein.

The method can also be further characterized by, for example, the identity of the nucleo-functional polymer, the identity of the electro-functional polymer, physical characteristics of the hydrogel formed, and other features described herein below.

Second Method—Supporting Retinal Tissue

Another aspect of the invention provides a method of supporting retinal tissue in the eye of a subject, the method comprising: (a) administering to the vitreous cavity of an eye of the subject an effective amount of nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group.

The method can be further characterized by, for example, the identity of the subject. In certain embodiments, subject has a physical discontinuity in the retinal tissue. In certain embodiments, the physical discontinuity is a tear in the retinal tissue, a break in the retinal tissue, or a hole in the retinal tissue. In other embodiments, the subject has undergone surgery for a macular hole, has undergone surgery to remove at least a portion of a epiretinal membrane, or has undergone a vitrectomy for vitreomacular traction. In other embodiments, the subject has a detachment of at least a portion of the retinal tissue. The retinal detachment may be, for example, a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to support the retinal tissue, such as an amount that upon formation of the hydrogel, the hydrogel contacts the retinal tissue.

The method can also be further characterized by, for example, the identity of the nucleofunctional polymer, the identity of the electro-functional polymer, physical characteristics of the hydrogel formed, and other features described herein below.

Third Method—Treating a Subject with a Retinal Detachment

Another aspect of the invention provides a method of treating a subject with a retinal detachment, the method comprising: (a) administering a nucleo-functional polymer and an electrofunctional polymer to the vitreous cavity of an eye of the subject with a detachment of at least a portion of retinal tissue; and (b) allowing the nucleo-functional polymer and the electro-functional polymer to react to form a hydrogel in the vitreous cavity; wherein the hydrogel supports the retinal tissue during reattachment of the portion of the retinal tissue, the nucleo-functional polymer is a biocompatible polymer containing a plurality of thio-functional groups —$R^1$—SH wherein R is an ester-containing linker, and the electro-functional polymer is a biocompatible polymer containing at least one thiol-reactive group.

The method can be further characterized by, for example, the nature of the retinal detachment. In certain embodiments, the retinal detachment is a rhegmatogenous retinal detachment. In other embodiments, the subject has tractional retinal detachment or serous retinal detachment.

The nucleo-functional polymer and an electro-functional polymer are administered to the eye of the subject in an amount effective to support the retinal tissue, thereby facilitating treatment of the retinal detachment.

The method can also be further characterized by, for example, the identity of the nucleofunctional polymer, the identity of the electro-functional polymer, physical characteristics of the hydrogel formed, and other features described herein below.

Fourth Method—Treating Hypotony

Another aspect of the invention provides a method of treating a subject with low pressure in the eye (i.e., hypotony), the method comprising: (a) administering an effective amount of a nucleo-functional polymer and an electro-functional polymer to the vitreous cavity of an eye of the subject; and (b) allowing the nucleo-functional polymer and the electro-functional polymer to react to form a hydrogel in the vitreous cavity; to thereby treat the subject with low pressure in the eye, wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group. In certain embodiments, the method causes an increase in pressure of at least about 1 mmHg, 2 mmHg, 5 mmHg, 7 mmHg, or 10 mmHg in the eye of the subject.

In certain embodiments, the subject suffers from a choroidal effusion (e.g., a serous choroidal effusion or hemorrhagic choroidal effusion).

The method can also be further characterized by, for example, the identity of the nucleofunctional polymer, the identity of the electro-functional polymer, physical characteristics of the hydrogel formed, and other features described herein below.

Fifth Method—Treating Choroidal Effusion

Another aspect of the invention provides a method of treating a choroidal effusion, the method comprising: (a) administering an effective amount of a nucleo-functional polymer and an electro-functional polymer to an eye of the subject having a choroidal effusion; and (b) allowing the nucleo-functional polymer and the electro-functional polymer to react to form a hydrogel; to thereby treat the choroidal effusion, wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiolreactive group.

In certain embodiments, the choroidal effusion is a serous choroidal effusion or hemorrhagic choroidal effusion.

In certain embodiments, the method causes an increase in pressure of at least about 1 mmHg, 2 mmHg, 5 mmHg, 7 mmHg, or 10 mmHg in the eye of the subject.

The method can also be further characterized by, for example, the identity of the nucleofunctional polymer, the identity of the electro-functional polymer, physical characteristics of the hydrogel formed, and other features described herein below.

Sixth Method—Improving Visual Performance

Another aspect of the invention provides a method of improving visual performance in a patient suffering from a retinal detachment, the method comprising: (a) administering to the vitreous cavity of an eye of the subject an effective amount of nucleo-functional polymer and an electro-functional polymer; and (b) allowing the nucleo-functional polymer and the electrofunctional polymer to react to form a hydrogel in the vitreous cavity; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group.

The method can be further characterized by, for example, the identity of the subject. In certain embodiments, the subject may have suffered from a retinal detachment that is a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to support the retinal tissue, such as an amount that upon formation of the hydrogel, the hydrogel contacts the retinal tissue.

Visual performance pertains to the patient's overall vision quality and includes a patient's ability to see clearly, as well as ability to distinguish between an object and its background. One aspect of visual performance is visual acuity, which is a measure of a patient's ability to see clearly. Visual acuity can be assessed, for example, by using conventional "eye charts" in which visual acuity is evaluated by the ability to discern letters of a certain size, with five letters of a given size present on each line (see, e.g., the "ETDRS" eye chart described in the Murphy, R. P., CURRENT TECHNIQUES IN OPHTHALMIC LASER SURGERY, 3rd Ed., edited by L. D. Singerman, and G. Cascas, Butterworth Heinemann, 2000). Evaluation of visual acuity may also be achieved by measuring reading speed and reading time. Visual acuity may be measured to evaluate whether administration of a necrosis inhibitor and/or an apoptosis inhibitor to the affected eye preserves or permits improvement of visual acuity (e.g., to 20/40 vision or to 20/20 vision). In certain embodiments, a Snellen chart can be used to measure a patient's visual acuity, and the measurement can be taken under conditions that test low-contrast visual acuity or under conditions that test high-contrast visual acuity. Also, the visual acuity measurement can be taken under scotopic conditions, mesopic conditions, and/or photopic conditions.

Another aspect of visual performance is contrast sensitivity, which is a measure of the patient's ability to distinguish between an object and its background. The contrast sensitivity can be measured under various light conditions, including, for example, photopic conditions, mesopic conditions, and scotopic conditions. In certain embodiments, the contrast sensitivity is measured under mesopic conditions.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a two-line improvement in the patient's vision as measured using the Snellen chart. In certain other embodiments, the improvement in visual acuity is a one-line improvement in the patient's vision as measured using the Snellen chart.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions.

Results achieved by the methods can be characterized according to the patient's improvement in contrast sensitivity. For example, in certain embodiments, the improvement in contrast sensitivity is at least a 10%, 20%, 30%, 50%, 60%, 70%, 80%, 90%, or 100% improvement measured under mesopic conditions using an art-recognized test, such as a Holladay Automated Contrast Sensitivity System. In certain embodiments, the improvement in contrast sensitivity is at least a 10%, 20%, 30%, 50%, 60%, 70%, 80%, 90%, or 100% improvement measured under photopic conditions using an art-recognized test, such as a Holladay Automated Contrast Sensitivity System. In certain other embodiments, the improvement in contrast sensitivity is at least a 10%, 20%, 30%, 50%, 60%, 70%, 80%, 90%, or 100% improvement measured under mesopic conditions or scotopic conditions using an art-recognized test, such a Holladay Automated Contrast Sensitivity System.

Visual performance may also be measured by determining whether there is an increase in the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT); an improvement of the photoreceptor cell layer or its subdivisions as seen in the OCT; an improvement of visual field (e.g., by at least 10% in the mean standard deviation on the Humphrey Visual Field Test; an improvement of an electroretinograph (ERG), a measurement of the electrical response of the retina to light stimulation, (e.g., to increase ERG amplitude by at least 15%); and or preservation or improvement of multifocal ERG, which evaluates the response of the retina to multifocal stimulation and allows characterization of the function of a limited area of the retina.

Visual performance may also be measured by electrooculography (EOG), which is a technique for measuring the resting potential of the retina. EOG is particularly useful for the assessment of RPE function. EOG may be used to evaluate whether administration of a necrosis inhibitor and/or an apoptosis inhibitor to the retina of the affected eye preserves or permits improvement in, for example, the Arden ratio (e.g., an increase in Arden ratio of at least 10%).

Visual performance may also be assessed through fundus autofluorescence (AF) imaging, which is a clinical tool that allows evaluation of the interaction between photoreceptor cells and the RPE. For example, increased fundus AF or decreased fundus AF has been shown to occur in AMD and other ocular disorders. Fundus AF imaging may be used to evaluate whether administration of a necrosis inhibitor and/or an apoptosis inhibitor to the retina of the affected eye slows disease progression.

Visual performance may also be assessed by microperimetry, which monitors retinal visual function against retinal thickness or structure and the condition of the subject's fixation over time. Microperimetry may be used to assess whether administration of a necrosis inhibitor and/or an apoptosis inhibitor to the retina of the affected eye preserves or permits improvement in retinal sensitivity and fixation.

The method can also be further characterized by, for example, the identity of the nucleofunctional polymer, the identity of the electro-functional polymer, physical characteristics of the hydrogel formed, and other features described herein below.

Seventh Method—Supporting Tissue in or Adjacent to the Anterior Chamber of the Eye Another aspect of the invention provides a method of supporting tissue in or adjacent to the anterior chamber of the eye of a subject, the method comprising: (a) administering an effective amount of a nucleo-functional polymer and an electro-functional polymer to the anterior chamber of an eye of the subject; and (b) allowing the nucleo-functional polymer and the electro-functional polymer to react to form a hydrogel in the anterior chamber; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiol-reactive group. In certain embodiments, the method supports a graft in the anterior chamber of the eye. The hydrogel achieves supporting tissue in or adjacent to the anterior chamber of the eye by coming into contact with such tissue and optionally exerting a force (e.g., 0.1, 0.5, 1.0, or 2.0 N) against such tissue.

The method can also be further characterized by, for example, the identity of the nucleofunctional polymer, the identity of the electro-functional polymer, physical characteristics of the hydrogel formed, and other features described herein below.

Eighth Method—Maintaining or Expanding a Nasolacrimal Duct

Another aspect of the invention provides a method of maintaining or expanding a nasolacrimal duct in a subject, the method comprising: (a) administering an effective amount of a nucleo-functional polymer and an electro-functional polymer to a nasolacrimal duct in a subject; and (b) allowing the nucleo-functional polymer and the electro-functional polymer to react to form a hydrogel in the nasolacrimal duct; wherein the nucleo-functional polymer is a biocompatible polymer containing a plurality of thio-functional groups —$R^1$—SH wherein $R^1$ is an ester-containing linker, and the electro-functional polymer is a biocompatible polymer containing at least one thiolreactive group. The hydrogel achieves maintaining or expanding a nasolacrimal duct by coming into contact with such tissue and optionally exerting a force (e.g., 0.1, 0.5, 1.0, or 2.0 N) against such tissue.

The method can also be further characterized by, for example, the identity of the nucleofunctional polymer, the identity of the electro-functional polymer, physical characteristics of the hydrogel formed, and other features described herein below.

Injectable, Ocular Formulation for Forming a Hydrogel

Another aspect of the invention provides an injectable, ocular formulation for forming a hydrogel in the eye of a subject, the formulation comprising: (a) a nucleo-functional polymer that is a biocompatible polymer containing a plurality of thio-functional groups —$R^1$—SH wherein $R^1$ is an ester-containing linker; (b) an electro-functional polymer that is a biocompatible polymer containing at least one thiol-reactive group; and (c) a liquid pharmaceutically acceptable carrier for administration to the eye of a subject. The formulation can be further characterized by, for example, the identity of the nucleo-functional polymer, the identity of the electro-functional polymer, physical characteristics of the hydrogel formed, and other features described herein below.

General Features of the Methods and Injectable Ocular Formulation

General features of the methods and injectable ocular formulation are described below.

Features of the Hydrozel

The therapeutic methods and compositions for forming hydrogels can be further characterized according to features of the hydrogel. Exemplary features of the hydrogel include, for example, refractive index, transparency, density, gelation time, elastic modulus, viscosity (e.g., dynamic viscosity), biodegradation, and pressure generated by the hydrogen within the eye or other location into which the polymers for forming a hydrogel are inserted.

The hydrogel is formed by reaction of the nucleo-functional polymer and electrofunctional polymer, and the subsequent update of water from the subject (e.g., the subject's eye). In the more specific embodiment of a thiolated poly(vinyl alcohol) polymer as the nucleo-functional polymer and a poly(ethylene glycol) (PEG) containing thiol-reactive groups as the electrofunctional polymer, the hydrogel is formed by a cross-linking reaction of thiolated poly(vinyl alcohol) (TPVA) with poly(ethylene glycol) (PEG) containing thiol-reactive groups. The thiolated poly(vinyl alcohol) polymer can be prepared according to procedures described in the literature (see, for example, U.S. Patent Application Publication No. 2016/0009872, which is hereby incorporated by reference), whereby thiol groups are incorporated into poly(vinylalcohol) (PVA) by coupling thiol functionalities to the hydroxyl groups of the poly(vinyl alcohol), or through use of protected thiol functionalities with subsequent deprotection. Certain poly(ethylene glycol) polymers containing thiol-reactive groups (e.g., an acrylate, methacrylate, maleimidyl, or N-hydroxysuccinimidyl) have been described in the literature (see, for example, U.S. Patent Application Publication No. 2016/0009872).

Crosslinking of the thiolated poly(vinyl alcohol) and the poly(ethylene glycol) containing thiol-reactive groups occurs through a Michael addition, without formation of byproducts and does not require use of toxic initiators or a UV source. Further, there is no medically significant release of heat during the cross-linking reaction. Moreover, a freeze-thaw process is not required, as is commonly used to form poly(vinyl alcohol) hydrogels. Therefore, the nucleofunctional polymer and electro-functional polymer can be mixed easily in an operating room. Also, to the extent there are any unreacted nucleo-functional polymer and/or electro-functional polymer, the molecular weight of these components is desirably low enough that they will be readily cleared from the eye by natural processes.

Formation of a thiolated poly(vinyl alcohol) from PVA (in which some of the hydroxyl groups of the PVA remain esterified as acetate groups), and then reaction of the thiolated poly(vinyl alcohol) with a poly(ethylene glycol) containing thiol-reactive groups is illustrated in the scheme below.

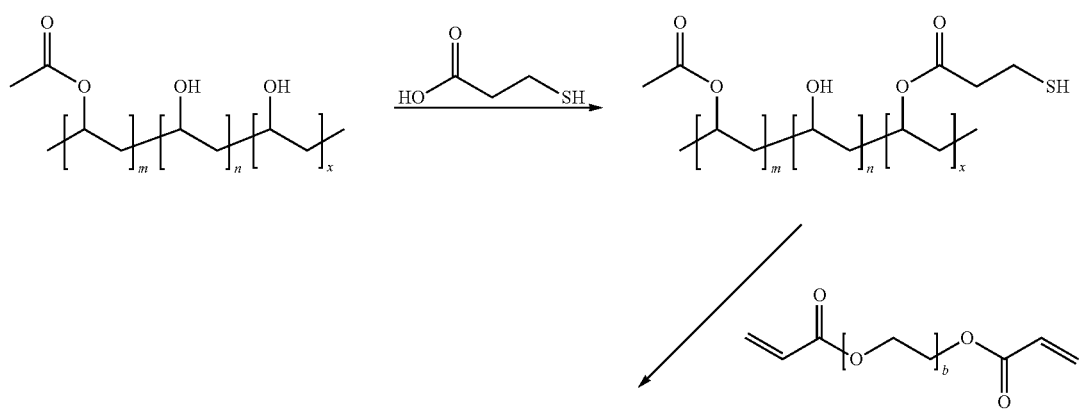

-continued

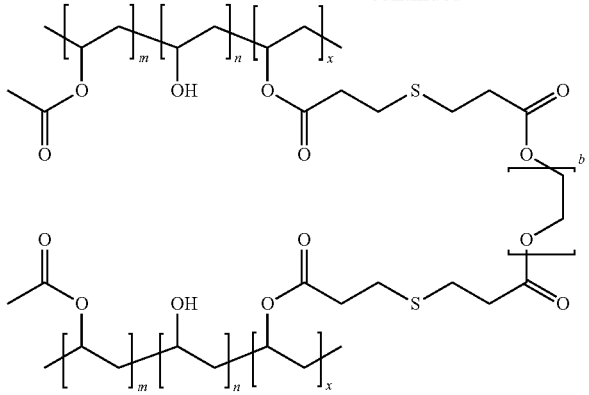

Refractive Index

The therapeutic methods and compositions can be characterized according to the refractive index of hydrogel formed. For example, in certain embodiments, the hydrogel has a refractive index in the range of from about 1.2 to about 1.5. In certain other embodiments, the hydrogel has a refractive index in the range of from about 1.3 to about 1.4. In certain other embodiments, the hydrogel has a refractive index in the range of from about 1.30 to about 1.35, or from about 1.31 to about 1.36.

Transparency

The therapeutic methods and compositions can be characterized according to the transparency of the hydrogel formed. For example, in certain embodiments, the hydrogel has a transparency of at least 95% for light in the visible spectrum when measured through hydrogel having a thickness of 2 cm. In certain embodiments, the hydrogel has a transparency of at least 90%, 94%, or 98% for light in the visible spectrum when measured through hydrogel having a thickness of 2 cm.

Density

The therapeutic methods and compositions can be characterized according to the density of the hydrogel formed. For example, in certain embodiments, the hydrogel has a density in the range of about 1 to about 1.5 g/mL. In certain other embodiments, the hydrogel has a density in the range of about 1 to about 1.2 g/mL, about 1.1 to about 1.3 g/mL, about 1.2 to about 1.3 g/mL, or about 1.3 to about 1.5 g/mL. In certain other embodiments, the hydrogel has a density in the range of about 1 to about 1.2 g/mL. In certain other embodiments, the hydrogel has a density in the range of about 1 to about 1.1 g/mL.

Gelation Time

The therapeutic methods and compositions can be characterized according to the gelation time of the hydrogel (i.e., how long it takes for the hydrogel to form once the nucleo-functional polymer has been combined with the electro-functional polymer). For example, in certain embodiments, the hydrogel has a gelation time from about 1 minute to about 30 minutes after combining the nucleo-functional polymer and the electro-functional polymer. In certain embodiments, the hydrogel has a gelation time from about 5 minutes to about 30 minutes after combining the nucleo-functional polymer and the electro-functional polymer. In certain other embodiments, the hydrogel has a gelation time from about 5 minutes to about 20 minutes after combining the nucleo-functional polymer and the electro-functional polymer. In certain other embodiments, the hydrogel has a gelation time from about 5 minutes to about 10 minutes after combining the nucleo-functional polymer and the electro-functional polymer. In certain other embodiments, the hydrogel has a gelation time of less than about 1, 5, 10, 15, 20, 25, 30, 35, 40, 45, 50, 55 or 60 minutes.

Elastic Modulus

The therapeutic methods and compositions can be characterized according to the elastic modulus of the hydrogel formed. For example, in certain embodiments, the hydrogel has an elastic modulus in the range of from about 200 Pa to about 15 kPa at a temperature of 25° C. In certain embodiments, the hydrogel has an elastic modulus in the range of from about 600 Pa to about 7 kPa at a temperature of 25° C.

Dynamic Viscosity

The therapeutic methods and compositions can be characterized according to the dynamic viscosity of the hydrogel formed. For example, in certain embodiments, the hydrogel has a dynamic viscosity in the range of about 20 to 60 cP at a temperature of 20° C.

Biodegradation

The therapeutic methods and compositions can be characterized according whether the hydrogel is biodegradable. Accordingly, in certain embodiments, the hydrogel is biodegradable. A biodegradable hydrogel can be further characterized according to the rate at which the hydrogel undergoes biodegradation from the eye. In certain embodiments, the hydrogel undergoes complete biodegradation from the eye of the subject within about 2 weeks to about 8 weeks. In certain embodiments, the hydrogel undergoes complete biodegradation from the eye of the subject within about 3 weeks to about 5 weeks. In certain embodiments, the hydrogel undergoes complete biodegradation from the eye of the subject within about 4 months to about 6 months. In certain embodiments, the hydrogel undergoes complete biodegradation from the eye of the subject within about 3 days to about 7 days. In certain embodiments, the hydrogel undergoes complete biodegradation from the eye of the subject within 1, 2, 3, 4, 5, 6, 7, 8, 9, 10, 11, 12, 13, 14, 15, 16, 17, 18, 19, 20, 21, 22, 23, or 24 weeks. In certain embodiments, the hydrogel undergoes complete biodegradation from the eye of the subject within 1, 2, 3, 4, 5, 6, 7, 8, 9, 10, 11, 12, 13, 14, 15, 16, 17, 18, 19, 20, 21, 22, 23, or 24 months.

In certain embodiments, the hydrogel has a biodegradation half-life in the range of from about 4 days to about 20 days when disposed within the vitreous cavity of an eye. In certain embodiments, the hydrogel has a biodegradation half-life in the range of from about 1 month to about 2 months when disposed within the vitreous cavity of an eye.

In certain embodiments, the hydrogel has a biodegradation half-life in the range of from about 1 week to about 3 weeks when disposed within the vitreous cavity of an eye. In certain embodiments, the hydrogel has a biodegradation half-life in the range of from about 8 weeks to about 15 weeks when disposed within the vitreous cavity of an eye. In certain embodiments, the hydrogel has a biodegradation half-life of less than 1, 2, 3, 4, 5, 6, 7, 8, 9, 10, 11, 12, 13, 14, 15, 16, 17, 18, 19, 20, 21, 22, 23, or 24 weeks when disposed within the vitreous cavity of an eye. In certain embodiments, the hydrogel has a biodegradation half-life of less than 1, 2, 3, 4, 5, 6, 7, 8, 9, 10, 11, 12, 13, 14, 15, 16, 17, 18, 19, 20, 21, 22, 23, or 24 months when disposed within the vitreous cavity of an eye.

In yet other embodiments, the hydrogel turns into liquid after approximately 5 weeks at a temperature in the range of 20° C. to 25° C., or within from about 4 weeks to 10 weeks, including all values and ranges therein. In embodiments, the ester bonds remaining in the hydrogel may degrade at room temperature in solution, such as in a phosphate buffered saline solution. In embodiments, degradation may begin after a few days and the hydrogel may be almost fully degraded, that is they form soluble products and the hydrogel turns in to liquid at around five weeks at a temperature in the range of 20° C. to 25° C. The rate of degradation will depend on a number of parameters, including total crosslink density, number of ester linkages in the crosslinks and the specifics of the environment.

Deliberate inclusion of degradable constituents into the nucle-functional polymer and/or electro-functional polymer permits tuning of the degradability and longevity of these materials in their chosen application. Examples of degradable constituents can be in the crosslinks, or elsewhere and can include, for example, any molecule or group that contains an ester bond (e.g. carbamate, amide, carbonate, lactic acid, glycolic acid, caprolactone or others). In particular embodiments, the degradable elements may be incorporated at an amount in the range of 1 to 6 per crosslinker. Similarly, incorporation of other functional groups into the hydrogel, such as though modification of the poly(vinyl alcohol) or poly(ethylene glycol) provide further degrees of tuning of the properties of the hydrogel.

Pressure Generated Within the Eye

The therapeutic methods and compositions can be characterized according to the amount of pressured generated by the hydrogel in eye of the subject. For example, in certain embodiments, the hydrogel generates a pressure within the eye of less than 25 mmHg. In certain other embodiments, the hydrogel generates a pressure within the eye in the range of from about 10 mmHg to about 25 mmHg. In certain other embodiments, the hydrogel generates a pressure within the eye of about 15, 16, 17, 18, 19, 20, 21, 22, 23, 24, or 25 mmHg.

It is contemplated that upon initial formation of the hydrogel in the eye of a subject, the hydrogel will be in a hyperosmotic state, where the concentration of hydrogel is such that additional fluid is pulled in (if available) by the gel to swell it. This approach allows the injected hydrogel to be filled passively to the size of the cavity, and then pull in additional water to exert an active swelling pressure on the interior of the eye suitable for the tamponade affect. The extent of the hyperosmotic state would be tunable using the concentration of the active ingredients. The source of the water in vivo would be the natural aqueous production in the eye, which is known to be produced at a rate of approximately 2-3 μL/min.

Features of the Nucleo-Functional Polymer

The therapeutic methods and compositions for forming a hydrogel can be characterized according to features of the nucleo-functional polymer. Accordingly, in certain embodiments, the nucleo-functional polymer is a biocompatible polymer selected from a polyalkylene and polyheteroalkylene polymer each being substituted by (i) a plurality of thio-functional groups —$R^1$—SH (where, as described above, $R^1$ is an ester-containing linker), and optionally (ii) one or more hydroxyl, alkyl ester, hydroxyalkyl ester, or amide groups. In certain embodiments, the nucleofunctional polymer is a biocompatible polyalkylene polymer substituted by (i) a plurality of thiofunctional groups —$R^1$—SH and (ii) a plurality of groups selected from the group consisting of hydroxyl, alkyl ester, hydroxyalkyl ester, and amide. In certain embodiments, the nucleo-functional polymer is a biocompatible polymer selected from poly(vinyl alcohol), poly(vinyl alcohol methacrylate), polyacrylamide, or poly(2-hydroxyethyl methacrylate), each being substituted by a plurality of thio-functional groups —$R^1$—SH. In certain embodiments, the nucleo-functional polymer is a biocompatible poly(vinyl alcohol) polymer substituted by a plurality of thio-functional groups —$R^1$—SH. In certain embodiments, the nucleo-functional polymer is a biocompatible, partially hydrolyzed poly(vinyl alcohol) polymer substituted by a plurality of thio-functional groups —$R^1$—SH. In certain embodiments, the nucleo-functional polymer is a biocompatible, partially hydrolyzed poly(vinyl alcohol) polymer substituted by a plurality of thio-functional groups —$R^1$—SH, wherein the degree of hydrolysis of the partially hydrolyzed poly(vinyl alcohol) polymer is at least 85%, 88%, 90%, 92%, 95%, 97%, 98%, or 99%. In certain embodiments, the nucleo-functional polymer is a biocompatible, partially hydrolyzed poly(vinyl alcohol) polymer substituted by a plurality of thiofunctional groups —$R^1$—SH, wherein the degree of hydrolysis of the partially hydrolyzed poly(vinyl alcohol) polymer is at least 95%. In certain embodiments, the nucleo-functional polymer is a biocompatible, partially hydrolyzed poly(vinyl alcohol) polymer substituted by a plurality of thiofunctional groups —$R^1$—SH, wherein the degree of hydrolysis of the partially hydrolyzed poly(vinyl alcohol) polymer is at least 98%.

In certain embodiments, the thio-functional group —$R^1$—SH is —OC(O)—($C_1$-$C_6$ alkylene)-SH. In certain embodiments, the thio-functional group —$R^1$—SH is —OC(O)—($CH_2CH_2$)—SH.

As described in the literature, poly(vinyl alcohol) is prepared by first polymerizing vinyl acetate to produce poly(vinyl acetate), and then the poly(vinyl acetate) is subjected to hydrolytic conditions to cleave the ester bond of the acetate group leaving only a hydroxyl group bound to the polymer backbone. Depending on the hydrolytic conditions used to cleave the ester bond of the acetate group, the resulting polymer product may still contain some acetate groups. That is, not all the acetate groups on the polymer are cleaved. For this reason, per common nomenclature used in the literature, the poly(vinyl alcohol) can be further characterized according to whether it is (a) fully hydrolyzed (i.e., all the acetate groups from the starting poly(vinyl acetate) starting material that have been converted to hydroxyl groups)) or (b) partially hydrolyzed (i.e., where some percentage of acetate groups from the poly(vinyl acetate) starting material have not been converted to hydroxyl groups). A partially hydrolyzed poly(vinyl alcohol) can be referred to as a poly(vinyl alcohol-covinyl acetate)). Per common usage in the literature, a poly(vinyl alcohol) that is partially hydrolyzed can be characterized according to the degree of hydrolysis (i.e., the percentage of acetate groups from the starting poly(vinyl acetate) starting material that have been converted to hydroxyl groups), such as greater than about 70%, 75%, 80%, 81%, 82%, 83%, 84%, 85%, 86%, 87%, 88%, 89%, 90%, 91%, 92%, 93%, 94%, 95%, 96%, 97%, 98%, or 99%. In certain embodiments, the degree of hydrolysis is in the range of from about 75% to about 95%, about 80% to about 95%, about 80% to about 90%, about 80% to about 85%, about 85% to about 95%, or about 85% to about 90%. For clarity, the term "poly(vinyl alcohol)" used herein encompasses both (a) fully hydrolyzed (i.e., all the acetate groups from the starting poly(vinyl acetate) starting material have been converted to hydroxyl groups)) and (b) partially hydrolyzed (i.e., where some percentage of acetate groups from the poly(vinyl acetate) starting material have not been converted to hydroxyl groups) material.

In certain embodiments, the nucleo-functional polymer is a biocompatible poly(vinyl alcohol) polymer comprising:

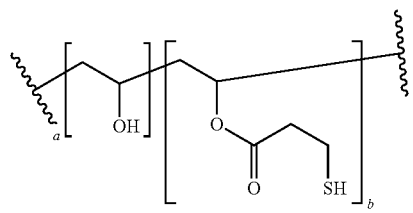

wherein a is an integer from 1-20 and b is an integer from 1-20.

In certain embodiments, the nucleo-functional polymer is a biocompatible poly(vinyl alcohol) polymer comprising:

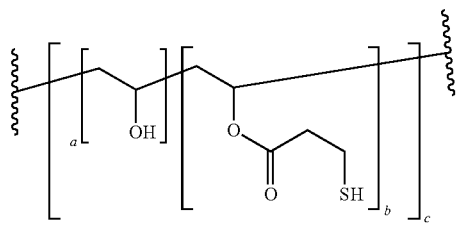

wherein a is an integer from 1-20, b is an integer from 1-20, and c is an integer from about 20 to about 500.

The nucleo-functional polymer may be further characterized according to its molecular weight, such as the weight-average molecular weight of the polymer. In certain embodiments, the nucleo-functional polymer has a weight-average molecular weight in the range of from about 500 g/mol to about 1,000,000 g/mol. In certain embodiments, the nucleo-functional polymer has a weight-average molecular weight in the range of from about 2,000 g/mol to about 500,000 g/mol. In certain embodiments, the nucleo-functional polymer has a weight-average molecular weight in the range of from about 4,000 g/mol to about 30,000 g/mol. In certain embodiments, the nucleofunctional polymer has a weight-average molecular weight less than about 200,000 g/mol or less than about 100,000 g/mol. In certain embodiments, the nucleo-functional polymer has a weight-average molecular weight in the range of from about 26,000 g/mol to about 32,000 g/mol. In certain embodiments, the nucleo-functional polymer has a weight-average molecular weight of about 29,000 g/mol. In certain embodiments, the nucleo-functional polymer has a weight-average molecular weight of about 30,000 g/mol. In certain embodiments, the nucleo-functional polymer has a weight-average molecular weight in the range of from about 45,000 g/mol to about 55,000 g/mol. In certain embodiments, the nucleo-functional polymer has a weight-average molecular weight of about 50,000 g/mol.

In a more specific embodiment, the nucleo-functional polymer is a thiolated poly(vinyl alcohol) that has been fully hydrolyzed or partially hydrolyzed (e.g., hydrolysis of about 75% or more, including all values and ranges from 75% to 99.9%, including 75%, 80%, 85%, 90%, 95%, 96%, 97%, 98%, 99%, etc.). The thiolated poly(vinyl alcohol) may be further characterized according to its molecular weight, such as where the thiolated poly(vinyl alcohol) has a weight average molecular weight (Mw) the range of 2 kDa to 2,000,000 kDa, including all values and ranges therein, and such as 2 kDa to 1,000,000 kDa, 2 kDa to 200 kDa, and 30 kDa to 50 kDa, etc. The thiolated poly(vinyl alcohol) may be provided in a solution, dissolved in water or other solvents (including, but not limited to, dimethyl sulfoxide (DMSO) or dimethylformamide (DMF)) at any viable concentration and preferably at a concentration in the range of 0.0001 wt % to 50 wt %, including all values and increments therein.

The thiolated poly(vinyl alcohol) can be prepared by reacting a range of thiol containing functional groups with poly(vinyl alcohol), as further described in U.S. Patent Application Publication No. 2016/0009872, which is hereby incorporated by reference. In certain embodiments, thiolated poly(vinyl alcohol) is prepared by reacting (a) a compound having a thiol functionality and at least one hydroxyl-reactive group, such as, for example, a carboxyl group, represented by HS—R—CO$_2$H, where R may include an alkane, unsaturated ether, or ester group, and R includes from 1 to 20 carbons, with (b) a poly(vinyl alcohol).

In other more specific embodiments, the thiolated poly (vinyl alcohol) comprises the following fragment:

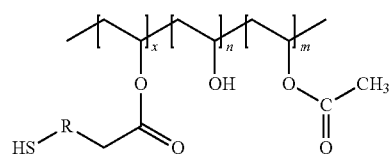

wherein R includes 1 to 20 carbons and may be an alkane, saturated ether or ester, and the individual units are randomly distributed along the length of the poly(vinyl alcohol) chain. X is in the range of 0.1-10%, n is in the range of 80-99.9%, indicating the level of hydrolysis of the poly (vinyl alcohol) polymer and allowing for water solubility of the polymer and m, the amount of non-hydrolyzed acetate groups, is in the range 0.1-20%.

The amount of thiol groups on the poly(vinyl alcohol) can be controlled by the number of hydroxyl groups on the poly(vinyl alcohol) that undergo reaction with the thiolating agent to generate the thiolated poly(vinyl alcohol). In certain embodiments, the amount of thiol functional groups on the poly(vinyl alcohol) may be characterized according to the molar ratio of thiol functional groups to poly(vinyl alcohol) polymer, such as from about 0.1:1 to about 10.0:1, including all values and ranges therein. Furthermore, the amount of thiol groups on the poly(vinyl alcohol) can be regulated by the reaction temperature and reaction time used when reacting the thiolating agent with the poly(vinyl alcohol) to form the thiolated poly(vinyl alcohol). In certain embodiments, the reaction temperature may be in the range of 40° C. to 95°

C., and reaction time may be in the range of 5 hours to 48 hours, including all values and ranges therein. Of course, cooler reaction temperatures may be utilized as well, such as in the range of 20° C. up to 40° C.

More generally, the nucleo-functional polymer containing a plurality of thio-functional groups can be prepared based on procedures described in the literature, such as U.S. Patent Application 2016/0009872 in which a polymer having nucleophilic groups (e.g., hydroxyl groups) is reacted with a thiol-containing compound so that resulting polymer contains a thiol group bound to the polymer backbone via a linker.

Features of the Electro-Functional Polymer

The therapeutic methods and compositions for forming a hydrogel can be characterized according to features of the electro-functional polymer. Accordingly, in certain embodiments, the electro-functional polymer is a biocompatible polymer selected from a polyalkylene and polyheteroalkylene polymer each being substituted by at least one thiol-reactive group. In certain embodiments, the electro-functional polymer is a biocompatible polyheteroalkylene polymer substituted by at least one thiol-reactive group. In certain embodiments, the electro-functional polymer is a biocompatible poly(oxyalkylene) polymer substituted by at least one thiol-reactive group. In certain embodiments, the electro-functional polymer is a biocompatible poly(ethyleneglycol) polymer substituted by at least one thiol-reactive group.

In certain embodiments, the thiol-reactive group is an alpha-beta unsaturated ester, maleimidyl, or

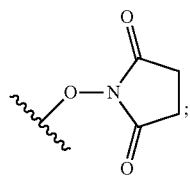 [SMILES: *ON1C(=O)CCC1=O]

each of which is optionally substituted by one or more occurrences of alkyl, aryl, or aralkyl. In certain embodiments, the thiol-reactive group is an alpha-beta unsaturated ester optionally substituted by one or more occurrences of alkyl, aryl, or aralkyl. In certain embodiments, the thiol-reactive group is —OC(O)CH=CH$_2$.

In certain embodiments, the electro-functional polymer has the formula:

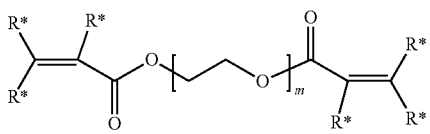

wherein R* is independently for each occurrence hydrogen, alkyl, aryl, or aralkyl; and m is an integer in the range of 5 to 15,000. In certain embodiments, R* is hydrogen. In yet other embodiments, m is an integer in the range of from about 20 to about 100, about 100 to about 500, about 500 to about 750, about 750 to about 1,000, about 1,000 to about 2,000, about 2,000 to about 5,000, about 5,000 to about 7,500, about 7,500 to about 10,000, about 10,000 to about 12,500, about 12,500 to about 15,000.

The electro-functional polymer may be further characterized according to its molecular weight, such the weight-average molecular weight of the polymer. Accordingly, in certain embodiments, the electro-functional polymer has a weight-average molecular weight in the range of from about 500 g/mol to about 1,000,000 g/mol. In certain embodiments, the electro-functional polymer has a weight-average molecular weight in the range of from about 1,000 g/mol to about 100,000 g/mol. In certain embodiments, the electro-functional polymer has a weight-average molecular weight in the range of from about 2,000 g/mol to about 8,000 g/mol. In certain embodiments, the electro-functional polymer has a weight-average molecular weight less than about 200,000 g/mol or less than about 100,000 g/mol. In certain embodiments, the electro-functional polymer has a weight-average molecular weight in the range of from about 3,000 g/mol to about 4,000 g/mol. In certain embodiments, the electro-functional polymer has a weight-average molecular weight in the range of from about 3,200 g/mol to about 3,800 g/mol. In certain embodiments, the electro-functional polymer has a weight-average molecular weight of about 3,500 g/mol.

The electro-functional polymer may be a straight-chain polymer or a branched chain polymer. In yet other embodiments, the electro-functional polymer may be a multi-arm polymer described in U.S. Pat. No. 9,072,809, which is hereby incorporated by reference, such as pentaerythritol polyethylene glycol maleimide (4ARM-PEG-MAL) (molecular weight selected from about 5,000 to about 40,000, e.g., 10,000 or 20,000), pentaerythritol polyethylene glycol succinimidyl succinate (4ARM-PEG-SS) (molecular weight selected from about 5,000 to about 40,000, e.g., 10,000 or 20,000), pentaerythritol polyethylene glycol succinimidyl glutarate (4ARMPEG-SG) (molecular weight selected from about 5,000 to about 40,000, e.g., 10,000 or 20,000), pentaerythritol polyethylene glycol succinimidyl glutaramide (4ARM-PEG-SGA) (molecular weight selected from about 5,000 to about 40,000, e.g., 10,000 or 20,000), hexaglycerin polyethylene glycol succinimidyl succinate (8ARM-PEG-SS) (molecular weight selected from about 5,000 to about 40,000, e.g., 10,000 or 20,000), hexaglycerin polyethylene glycol succinimidyl glutarate (8ARM-PEG-SG) (molecular weight selected from about 5,000 to about 40,000, e.g., 10,000, 15,000, 20,000, or 40,000), hexaglycerin polyethylene glycol succinimidyl glutaramide (8ARM-PEG-SGA) (molecular weight selected from about 5,000 to about 40,000, e.g., 10,000, 15,000, 20,000, or 40,000), tripentaerythritol polyethylene glycol succinimidyl succinate (8ARM(TP)-PEG-SS) (molecular weight selected from about 5,000 to about 40,000, e.g., 10,000 or 20,000), tripentaerythritol polyethylene glycol succinimidyl glutarate (8ARM(TP)-PEG-SG) (molecular weight selected from about 5,000 to about 40,000, e.g., 10,000, 15,000, 20,000, or 40,000), or tripentaerythritol polyethylene glycol succinimidyl glutaramide (8ARM(TP)-PEG-SGA) (molecular weight selected from about 5,000 to about 40,000, e.g., 10,000, 15,000, 20,000, or 40,000).

In another more specific embodiment, the electro-functional polymer may be a poly(ethylene glycol) end-capped with at least two thiol-reactive groups. The poly(ethylene glycol) may be linear, branched, a dendrimer, or multi-armed. The thiol reactive group may be, for example, an acrylate, methacrylate, maleimidyl, haloacetyl, pyridyldithiol, or N-hydroxysuccinimidyl. An exemplary poly(ethylene glycol) end-capped with thiol-reactive groups may be represented by the formula Y—[—O—CH$_2$CH$_2$—]$_n$—O—Y wherein each Y is a thiol-reactive group, and n is, for example, in the range of 200 to 20,000. In another more specific embodiment, the electro-functional polymer may be $CH_2$=CHC(O)O—[—$CH_2CH_2$—O-]b-C(O)CH=$CH_2$, wherein b is, for example, in the range of about 200 to about 20,000. Alternatively or additionally to the linear embodiments depicted above, the poly(ethylene glycol) may be a dendrimer. For example, the poly(ethylene glycol) may be a 4 to 32 hydroxyl dendron. In further embodiments, the poly(ethylene glycol) may be multi-armed. In such embodiments, the poly(ethylene glycol) may be, for example, a 4, 6 or 8 arm and hydroxy-terminated. The molecular weight of the poly(ethylene glycol) may be varied, and in some cases one of the thiol-reactive groups may be replaced with other structures to form dangling chains, rather than crosslinks. In certain embodiments, the molecular weight (Mw) is less than 20,000, including all values and ranges from 200 to 20,000, such as 200 to 1,000, 1,000 to 10,000, etc. In addition, the degree of functionality may be varied, meaning that the poly(ethylene glycol) may be mono-functional, di-functional or multi-functional.

More generally, the electro-functional polymer can be purchased from commercial sources or prepared based on procedures described in the literature, such as by treating a nucleofunctional polymer with reagent(s) to install one or more electrophilic groups (e.g., by reacting polyethylene glycol with acrylic acid in an esterification reaction to form polyethylene glycol diacrylate).

Relative Amount of Nucleo-Functional Polymer and Electro-Functional Polymer

The therapeutic methods and compositions for forming a hydrogel can be characterized according to relative amount of nucleo-functional polymer and electro-functional polymer used. Accordingly, in certain embodiments, the mole ratio of (i) thio-functional groups —$R^1$—SH to (ii) thiol-reactive group is in the range of 10:1 to 1:10. In certain embodiments, the mole ratio of (i) thio-functional groups —$R^1$—SH to (ii) thiol-reactive groups is in the range of 5:1 to 1:1. In certain embodiments, the mole ratio of (i) thio-functional groups —$R^1$—SH to (ii) thiol-reactive groups is in the range of 2:1 to 1:1.

In a more specific embodiment, a thiolated poly (vinyl alcohol) and poly(ethylene glycol)-diacrylate are delivered at a ratio of functional groups (mmol/mmol) in the range of 2:1 to 0.5:1, including all values and ranges therein, and preferably 1:1. Furthermore, once combined the combination of the thiolated poly(vinyl alcohol) and the poly(ethylene glycol)-diacrylate are present in solution in the range of about 6 mg/mL to about 250 mg/mL, including all values and ranges therein, and preferably about 25 mg/mL to about 65 mg/mL, and sometimes about 45 mg/mL. The viscosity of the thiolated poly(vinyl alcohol) and the poly(ethylene glycol)-diacrylate, prior to crosslinking and gelation, is in the range of about 0.005 Pa*s to about 0.35 Pa*s, including all values and ranges therein, such as in the range of about 0.010 Pa*s to about 0.040 Pa*s, and sometimes about 0.028 Pa*s.

Administration Features of Nucleo-Functional Polymer and Electro-Functional Polymer The method may be further characterized according to whether the nucleo-functional polymer and the electro-functional polymer are administered together as a single composition to the vitreous cavity of the eye of the subject, or alternatively the nucleo-functional polymer and the electro-functional polymer are administered separately to the vitreous cavity of the eye of the subject. In certain embodiments, the nucleo-functional polymer and the electro-functional polymer are administered together as a single composition to the vitreous cavity of the eye of the subject. The single composition may further comprise, for example, a liquid pharmaceutically acceptable carrier for administration to the eye of a subject. In certain embodiments, the nucleo-functional polymer and the electro-functional polymer are administered together as a single, liquid aqueous pharmaceutical composition to the vitreous cavity of the eye of the subject.

In certain other embodiments, the nucleo-functional polymer and the electro-functional polymer are administered separately to the vitreous cavity of the eye of the subject. Even when administered separately, the nucleo-functional polymer may be administered as a liquid ocular formulation comprising a liquid pharmaceutically acceptable carrier for administration to the eye of a subject. This facilitates easy administration of the nucleo-functional polymer through surgical ports in the eye of the subject. Similarly, the electro-functional polymer may be administered as a liquid ocular formulation comprising a liquid pharmaceutically acceptable carrier for administration to the eye of a subject. This facilitates easy administration of the electro-functional polymer through surgical ports in the eye of the subject. Accordingly, in certain embodiments, the nucleo-functional polymer and the electro-functional polymer are administered separately to the vitreous cavity of the eye of the subject, wherein the nucleo-functional polymer is administered as a single, liquid aqueous pharmaceutical composition to the vitreous cavity of the eye of the subject, and the electro-functional polymer is administered as a single, liquid aqueous pharmaceutical composition to the vitreous cavity of the eye of the subject.

The liquid aqueous pharmaceutical composition may be further characterized according to, for example, pH, osmolality and presence and/or identity of salts. In certain embodiments, the liquid aqueous pharmaceutical composition has a pH in the range of about 7.1 to about 7.7. In certain embodiments, the liquid aqueous pharmaceutical composition has a pH in the range of about 7.3 to about 7.5. In certain embodiments, the liquid aqueous pharmaceutical composition has a pH of about 7.4. In certain embodiments, the liquid aqueous pharmaceutical composition further comprises an alkali metal salt. In certain embodiments, the liquid aqueous pharmaceutical composition further comprises an alkali metal halide salt, an alkaline earth metal halide salt, or a combination thereof. In certain embodiments, the liquid aqueous pharmaceutical composition further comprises sodium chloride. In certain embodiments, the liquid aqueous pharmaceutical composition further comprises sodium chloride, potassium chloride, calcium chloride, magnesium chloride, or a combination of two or more of the foregoing. In certain embodiments, the liquid aqueous pharmaceutical composition has an osmolality in the range of about 280 mOsm/kg to about 315 mOsm/kg. In certain embodiments, the liquid aqueous pharmaceutical composition has an osmolality in the range of about 280 mOsm/kg to about 300 mOsm/kg. In certain embodiments, the liquid aqueous pharmaceutical composition has an osmolality in the range of about 285 mOsm/kg to about 295 mOsm/kg. In certain embodiments, the liquid aqueous pharmaceutical composition has an osmolality of about 290 mOsm/kg.

A liquid formulation containing (i) a nucleo-functional polymer and/or the electro-functional polymer and (ii) a liquid pharmaceutically acceptable carrier for administration to the eye of a subject may be further characterized according to the viscosity of the formulation. In certain embodiments, the liquid formulation has a viscosity within 10%, 25%, 50%, 75%, 100%, 150%, 200%, or 300% of water. In certain other embodiments, the liquid formulation has a viscosity such that it can be administered through a needle having a gauge of less than or equal to 23 using a force of no more than 5N. In certain embodiments, the liquid formulation has a viscosity such that 1-2 mL of the liquid formulation can be administered within 3 minutes using a needle having a gauge of less than or equal to 23 using a force of no more than 5N.

In a more specific embodiment, a nucleo-functional polymer and/or the electro-functional polymer are provided in an aqueous pharmaceutical composition for administration to the eye. Such aqueous pharmaceutical compositions are desirably low viscosity liquids. In embodiments, the liquids exhibit a viscosity in the range of 0.004 Pa*s to 0.5 Pa*s, including all values and ranges therein, such as 0.010 Pa*s to 0.05 Pa*s. For example, an aqueous pharmaceutical composition may desirably comprise poly(ethylene glycol) diacrylate at a concentration of 3 mg/mL to 300 mg/mL, including all values and ranges therein, such as in the range of 10 mg/mL to 50 mg/mL, and even the more specific value of about 30 mg/mL. Another more specific embodiment is a poly(ethylene glycol) diacrylate aqueous solution having a viscosity in the range of 0.007 Pa*s to 0.5 Pa*s, including all values and ranges therein, such as in the range of 0.01 Pa*s to 0.05 Pa*s, or the more specific value of about 0.035 Pa*s. Another more specific embodiment is a thiolated poly(vinyl alcohol) aqueous solution containing the thiolated poly(vinyl alcohol) at a range of 10 mg/mL to 200 mg/mL, including all values and ranges therein, such as the range of 40 mg/mL to 80 mg/mL, and the more specific value of about 60 mg/mL. Another more specific embodiment is thiolated poly(vinyl alcohol) aqueous solution having a viscosity in the range of 0.004 Pa*s to 0.2 Pa*s, including all values and ranges therein, such as in the range of 0.010 Pa*s to 0.040 Pa*s, or the more specific value of about 0.020 Pa*s.

It is appreciated that the properties and gelation times of the in situ formed gels can be regulated by the concentration of thiolated poly(vinyl alcohol) and poly(ethylene glycol)-diacrylate, their ratio used for cross-linking and functionality (amount of thiol groups linked to poly(vinyl alcohol) and the amount of thiol reactive groups per poly(ethylene glycol) molecule). By changing the thiolated poly(vinyl alcohol) to poly(ethylene glycol) ratio, one can also regulate the fraction of dangling poly(ethylene glycol) chains that can be used to improve hydrogel's surface properties. Furthermore, mixing a blend of mono-functional and bi-functional poly(ethylene glycol) crosslinkers, wherein the functionality is the thiol reactive groups will allow the tuning of the crosslinking versus hydrophilicity of the hydrogel. Control of the length of the mono-functional and bi-functional crosslinker or the size of the starting poly(vinyl alcohol), allows modification of mechanical properties, swelling, lubricity, morphology, and hydrophilicity as well as frictional and wear properties. These features described in connection with thiolated poly(vinyl alcohol) and poly(ethylene glycol)-diacrylate apply generally for the broader scope of nucleo-functional polymers and electro-functional polymers described herein.

Additional Step of Removing Vitreous Humor from the Eye

The method may optionally further comprise the step of removing vitreous humor from the eye prior to administration of the nucleo-functional polymer and the electro-functional polymer.

III. Injectable Ocular Pharmaceutical Compositions

The invention provides pharmaceutical compositions comprising (i) a nucleo-functional polymer and/or an electro-functional polymer and (ii) a pharmaceutically acceptable carrier for administration to the eye. Preferably, the pharmaceutical composition is a liquid pharmaceutical composition. The pharmaceutically acceptable carrier may be water or any other liquid suitable for administration to the eye of a subject.

The pharmaceutical composition is sterile and may optionally contain a preservative, antioxidant, and/or viscosity modifier. Exemplary viscosity modifiers include, for example, acacia, agar, alginic acid, bentonite, carbomers, carboxymethylcellulose calcium, carboxymethylcellulose sodium, carrageenan, ceratonia, cetostearyl alcohol, chitosan, colloidal silicon dioxide, cyclomethicone, ethylcellulose, gelatin, glycerin, glyceryl behenate, guar gum, hectorite, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly(methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, sulfobutylether (3-cyclodextrin), tragacanth, xanthan gum, and derivatives and mixtures thereof. In some embodiments, the viscosity modifier is a bioadhesive or comprises a bioadhesive polymer.

In some embodiments, the concentration of the viscosity modifier in the pharmaceutical composition ranges from 0.1 to 20% by weight. In certain embodiments, the concentration of the viscosity modifier in the pharmaceutical composition ranges from 5 to 20% by weight. In certain embodiments, the concentration of the viscosity modifier in the pharmaceutical composition is less than 20%, less than 15%, less than 10%, less than 9%, less than 8%, less than 7%, less than 6%, less than 5%, less than 4%, less than 3%, less than 2%, less than 1.8%, less than 1.6%, less than 1.5%, less than 1.4%, less than 1.2%, less than 1%, less than 0.9%, less than 0.8%, less than 0.7%, less than 0.6%, less than 0.5%, less than 0.4%, less than 0.3%, less than 0.2%, or less than 0.1% by weight.

The pharmaceutical composition may be further characterized according to its viscosity. In certain embodiments, the viscosity of the pharmaceutical composition is less than 4000 cP, less than 2000 cP, less than 1000 cP, less than 800 cP, less than 600 cP, less than 500 cP, less than 400 cP, less than 200 cP, less than 100 cP, less than 80 cP, less than 60 cP, less than 50 cP, less than 40 cP, less than 20 cP, less than 10 cP, less than 8 cP, less than 6 cP, less than 5 cP, less than 4 cP, less than 3 cP, less than 2 cP, less than 1 cP. In some embodiments, the viscosity of the pharmaceutical composition is at least 4,000 cP, at least 2,000 cP, at least 1,000 cP, at least 800 cP, at least 600 cP, at least 500 cP, at least 400 cP, at least 200 cP, at least 100 cP, at least 80 cP, at least 60 cP, at least 50 cP, at least 40 cP, at least 20 cP, at least 10 cP, at least 8 cP, at least 6 cP, at least 5 cP, at least 4 cP, at least 3 cP, at least 2 cP, at least 1 cP. In certain embodiments, the viscosity of the pharmaceutical composition is about 4,000 cP, about 2,000 cP, about 1,000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP, about 1 cP. In some embodiments, the viscosity of the viscosity of the pharmaceutical composition is between about 5 cP and 50 cP.

The pharmaceutical composition may be further characterized according to its pH. In certain embodiments, the pharmaceutical composition has a pH in the range of from about 5 to about 9, or about 6 to about 8. In certain embodiments, the pharmaceutical composition has a pH in the range of from about 6.5 to about 7.5. In certain embodiments, the pharmaceutical composition has a pH of about 7.

In certain embodiments, the pharmaceutical composition contains water, and the formulation has a pH in the range of about 7.1 to about 7.7. In certain embodiments, the pharmaceutical composition contains water, and the formulation has a pH in the range of about 7.1 to about 7.6, about 7.1 to about 7.5, about 7.1 to about 7.4, about 7.2 to about 7.6, about 7.2 to about 7.5, about 7.2 to about 7.4, about 7.2 to about 7.3, about 7.3 to about 7.7, about 7.3 to about 7.6, about 7.3 to about 7.5, about 7.3 to about 7.4, about 7.4 to about 7.7, about 7.4 to about 7.6, or about 7.4 to about 7.5. In certain embodiments, the pharmaceutical composition contains water, and the formulation has a pH in the range of about 7.3 to about 7.5. In certain embodiments, the pharmaceutical composition contains water, and the formulation has a pH of about 7.4.

The pharmaceutical composition may be further characterized according to osmolality and the presence and/or identity of salts. For example, in certain embodiments, the pharmaceutical composition has an osmolality in the range of about 280 mOsm/kg to about 315 mOsm/kg. In certain embodiments, the pharmaceutical composition has an osmolality in the range of about 280 mOsm/kg to about 300 mOsm/kg. In certain embodiments, the pharmaceutical composition has an osmolality in the range of about 285 mOsm/kg to about 295 mOsm/kg. In certain embodiments, the pharmaceutical composition has an osmolality of about 290 mOsm/kg. In certain embodiments, the pharmaceutical composition further comprises an alkali metal salt. In certain embodiments, the pharmaceutical composition further comprises an alkali metal halide salt, an alkaline earth metal halide salt, or a combination thereof. In certain embodiments, the pharmaceutical composition further comprises sodium chloride. In certain embodiments, the pharmaceutical composition further comprises sodium chloride, potassium chloride, calcium chloride, magnesium chloride, or a combination of two or more of the foregoing.

IV. Kits for Use in Medical Applications

Another aspect of the invention provides a kit for treating a disorder. The kit comprises: i) instructions for achieving one of the methods described herein (e.g., method for contacting retinal tissue in the eye of a subject with a hydrogel, methods for supporting retinal tissue, and methods for treating a subject with a retinal detachment); and ii) an nucleo-functional polymer described herein and/or an electro-functional polymer described herein.

The description above describes multiple aspects and embodiments of the invention. The patent application specifically contemplates all combinations and permutations of the aspects and embodiments.

EXAMPLES

The invention now being generally described, will be more readily understood by reference to the following examples, which are included merely for purposes of illustration of certain aspects and embodiments of the present invention, and are not intended to limit the invention.

Example 1—Preparation and Characterization of an Exemplary Hydrogel

Hydrogel is formed by reaction of a thiolated poly(vinyl alcohol) (abbreviated TPVA) with a poly(ethylene glycol) diacrylate (abbreviated PEGDA). TPVA is prepared by an esterification reaction of PVA with 3-mercaptopropionic acid and characterized by $^1$H NMR. The formed TPVA contains pendant chains with ester bonds linking the thiol groups to the PVA backbone. The gelation reaction between TPVA and PEGDA proceeds at physiological conditions in an aqueous environment without radical initiators or irradiation.

Hydrogel Formation

Gelation time and elastic modulus (G') values for exemplary hydrogels are provided in Table 1. Rapid gelation time is important because a gelation time of several hours for cross-linking creates the risk of adverse medical events, such as sub-retinal migration which would be clinically catastrophic and lead to re-detachment.

TABLE 1

Gelation time and modulus for preliminary formulation

| Polymer conc, % [w/v] | 25° C. | | | 37° C. | | |
| --- | --- | --- | --- | --- | --- | --- |
| | Gel time [min] | G' [Pa] | G'' [Pa] | Gel time [min] | G' [Pa] | G'' [Pa] |
| 3.0 | 23.3 | 803 | 5 | 4.2 | 3607 | 480 |
| 4.5 | 9.2 | 6440 | 133 | 3.0 | 9860 | 280 |

Hydrogel Degradation

Degradation of the hydrogel is facilitated by the presence of ester groups in the hydrogel, which are easily hydrolysable and do not require the presence of enzymes for degradation to occur. The degradability and swellability of exemplary PVA-PEG hydrogels have been tested in 1×PBS at ambient temperature. Hydrogels at 3 wt % polymer solids started disintegrating after 18 days and completely solubilized after 35 days, as described in U.S. Patent Application Publication US 2016/0009872.

GPC has been used to analyze the initial products of the in vitro degradation process. A GPC chromatogram is provided in FIG. 1, which is labeled according to identified materials which include TPVA, PEGDA, and TVPA/PEGDA degradation products.

Example 2—Preparation and Characterization of Additional Exemplary Hydrogel

A hydrogel was formed by reaction of a thiolated poly (vinyl alcohol) (abbreviated TPVA) with a poly(ethylene glycol) diacrylate (abbreviated PEGDA). Physical properties of the hydrogel were analyzed, as described below.

Hydrozel Formation

To a polypropylene disposable cuvette was added 1 mL of a TPVA solution and 1 mL of a PEGDA solution, to thereby form a hydrogel premix. The hydrogel premix was placed in a static incubator at a temperature of 37° C. for approximately 8 minutes during which time gelation occurred, to thereby provide the test hydrogel.

Figure 2:
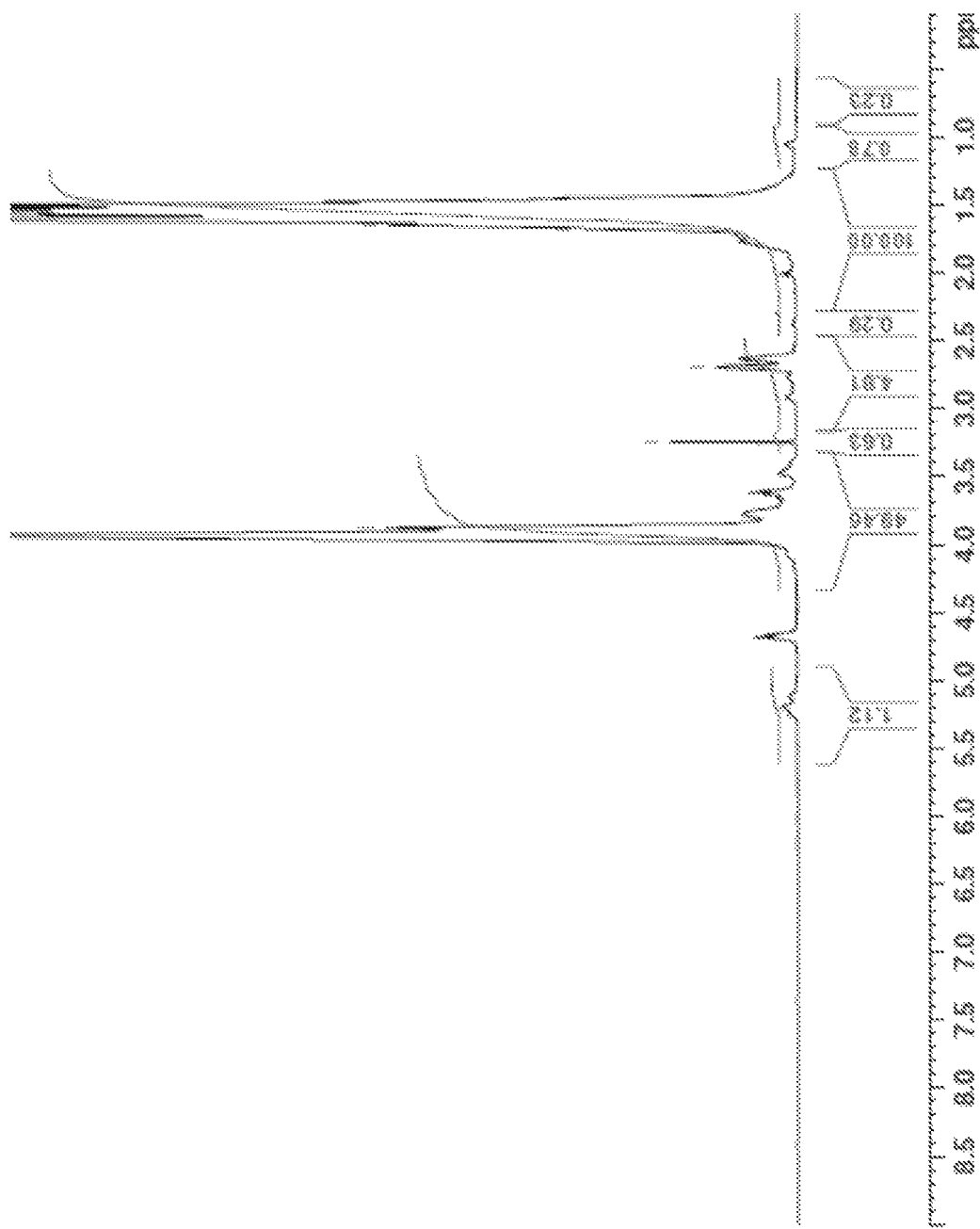
FIG. 2 is a $^1$H NMR ($D_2O$) spectrum of thiolated poly (vinyl alcohol) polymer, as further described in Example 2.

The TPVA solution was 6% w/w thiolated poly(vinyl alcohol) in phosphate buffered saline. The thiolated poly (vinyl alcohol) polymer is a poly(vinyl alcohol) in which approximately 4.3% of the hydroxyl groups on the polymer have been replaced with —OC(O)CH $2CH_2$—SH. A$^1$H NMR (D$_2$O) spectrum of the thiolated poly(vinyl alcohol) polymer is shown in FIG. 2, which as illustrated has a peak at 2.697 ppm (corresponding to two hydrogen atoms, which are believed to be due to the CH$_2$ group attached to the —SH group) and a peak at 3.889 ppm (corresponding to one hydrogen atom, which is believed to be due to the C—H hydrogen atom on the polymer backbone for carbon atoms bearing a hydroxyl group). The weight-average molecular weight of the thiolated poly(vinyl alcohol) polymer was calculated to be about 29,000 g/mol. The thiolated poly (vinyl alcohol) polymer was prepared from poly(vinyl alcohol) having a weight-average molecular weight of approximately 27,000 g/mol, based on procedures described in Ossipov et al. in *Macromolecules* (2008), vol. 41(11), pages 3971-3982.

The PEGDA solution is 3% w/w poly(ethylene glycol) diacrylate in phosphate buffered saline, wherein the poly (ethylene glycol) diacrylate has a weight average molecular weight of approximately 3,400 g/mol.

Analysis of UV-Visible Light Absorbance

Figure 3:
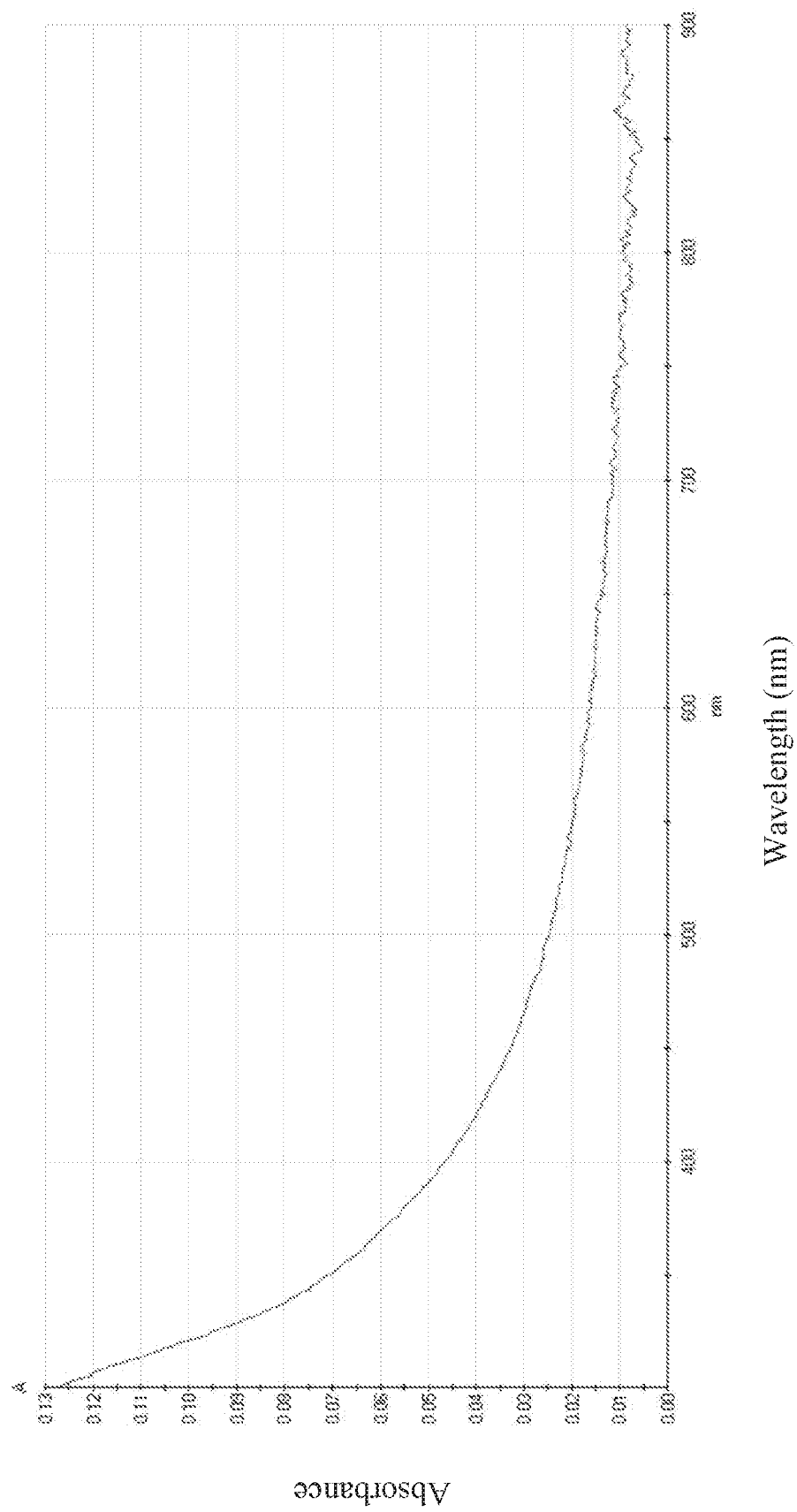
FIG. 3 is an absorbance spectrum taken on a sample of test hydrogel, as further described in Example 2.

UV-Visible light absorbance of the test hydrogel was analyzed by placing the test hydrogel in a Thermo Scientific Genesys 10S UV-Vis spectrophotometer and performing an absorbance scan across wavelengths ranging from 300 nm to 900 nm. Absorbance values for the test hydrogel were analyzed relative to absorbance values obtained using a blank cuvette containing distilled water. Results of the UV-Visible light absorbance scan of the test hydrogel are shown in FIG. 3.

Example 3—Refractive Index of Exemplary Hydrogel

An aliquot of the TPVA solution from Example 2 was mixed with an equal volume of an aliquot of the PEGDA solution from Example 2 to produce a hydrogel premix, and a 1 mL aliquot of the hydrogel premix was placed in a refractive index detector at a temperature of 37° C. The hydrogel was allowed to form. Once the hydrogel had formed, the refractive index of the hydrogel was measured and determined to be 1.3376. The instrument used to measure the refractive index was an Anton Paar Abbemat 200 Refractometer.

Example 4—Gelation Time and Elastic Modulus for Exemplary Hydrogel

Figure 4:
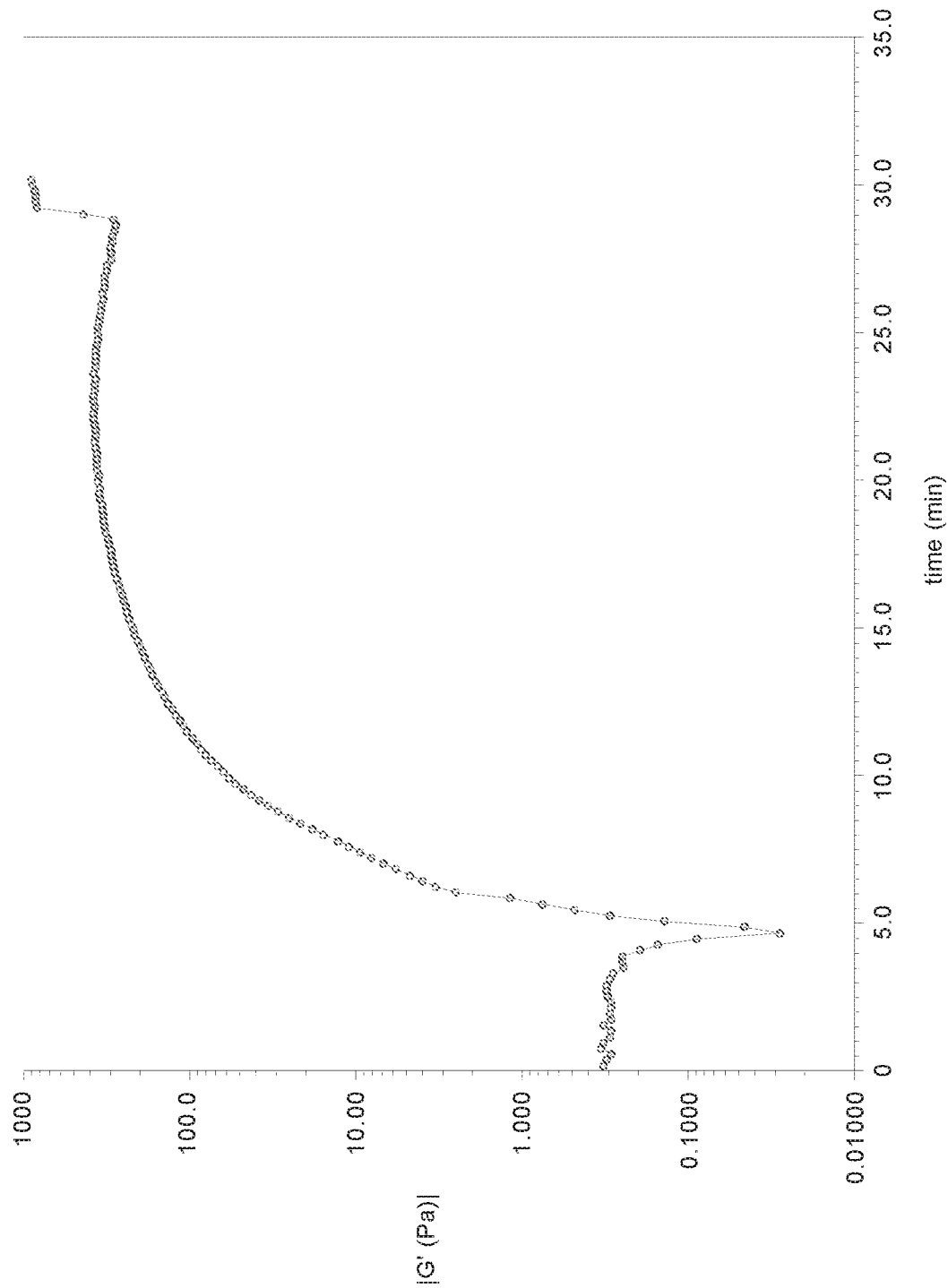
FIG. 4 is a graph showing results of a rheological properties analysis of test hydrogel, as further described in Example 4.

A 1 mL aliquot of the TPVA solution from Example 2 was mixed with a 1 mL aliquot of the PEGDA solution from Example 2, and the resulting mixture was placed onto the top platform of TA brand Advanced Rheometer AR 550. The top platform was maintained at a temperature of 37° C. A 60 mm 2° cone was applied to the mixture to provide the top geometry. Rheological properties of the mixture on the top platform were measured over a period of 30 minutes with oscillation at predetermined time points at a speed of 6.283 rad/s. Results are shown in FIG. 4.

Example 5—Transmission of Hydrogel Premix Through Surgical Port

Figure 5:
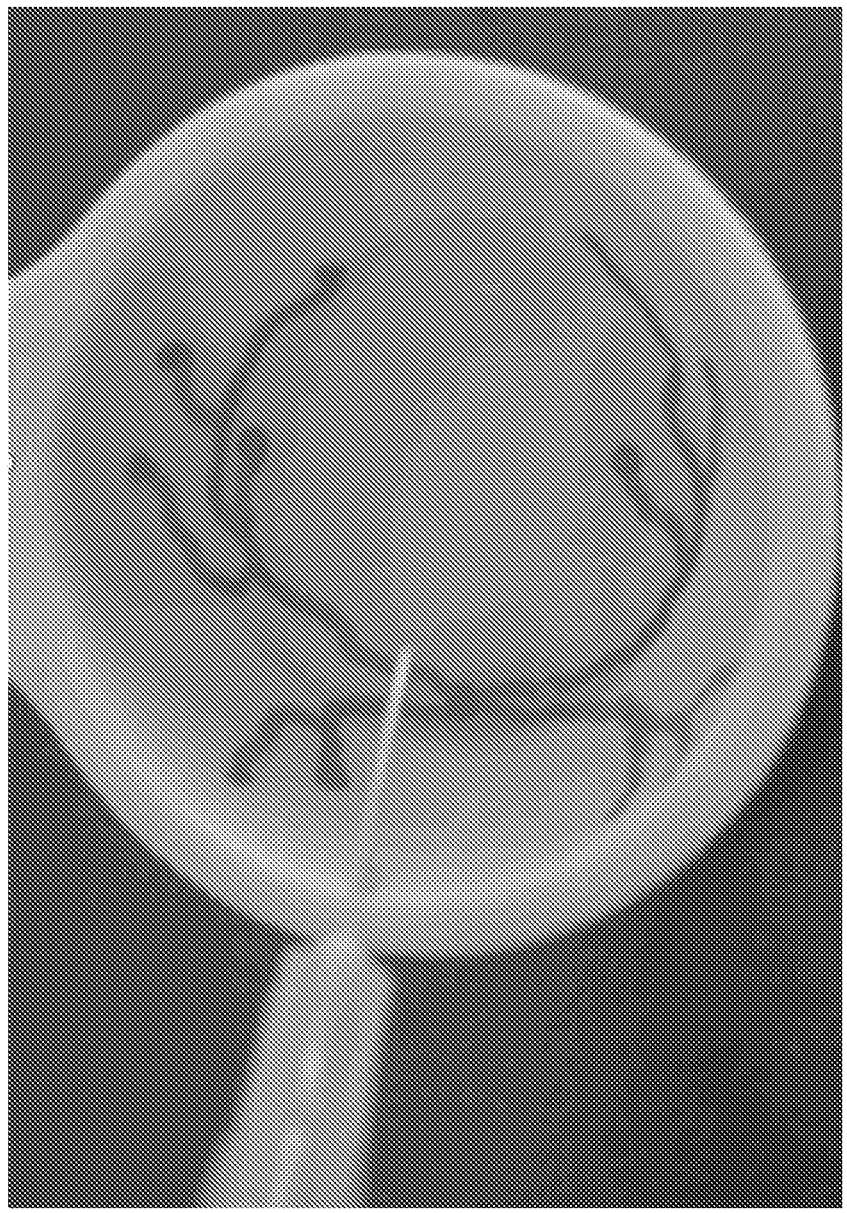
FIG. 5 is an illustration of hydrogel premix that has been dispensed from the syringe into a container, as further described in Example 5.
Figure 6:
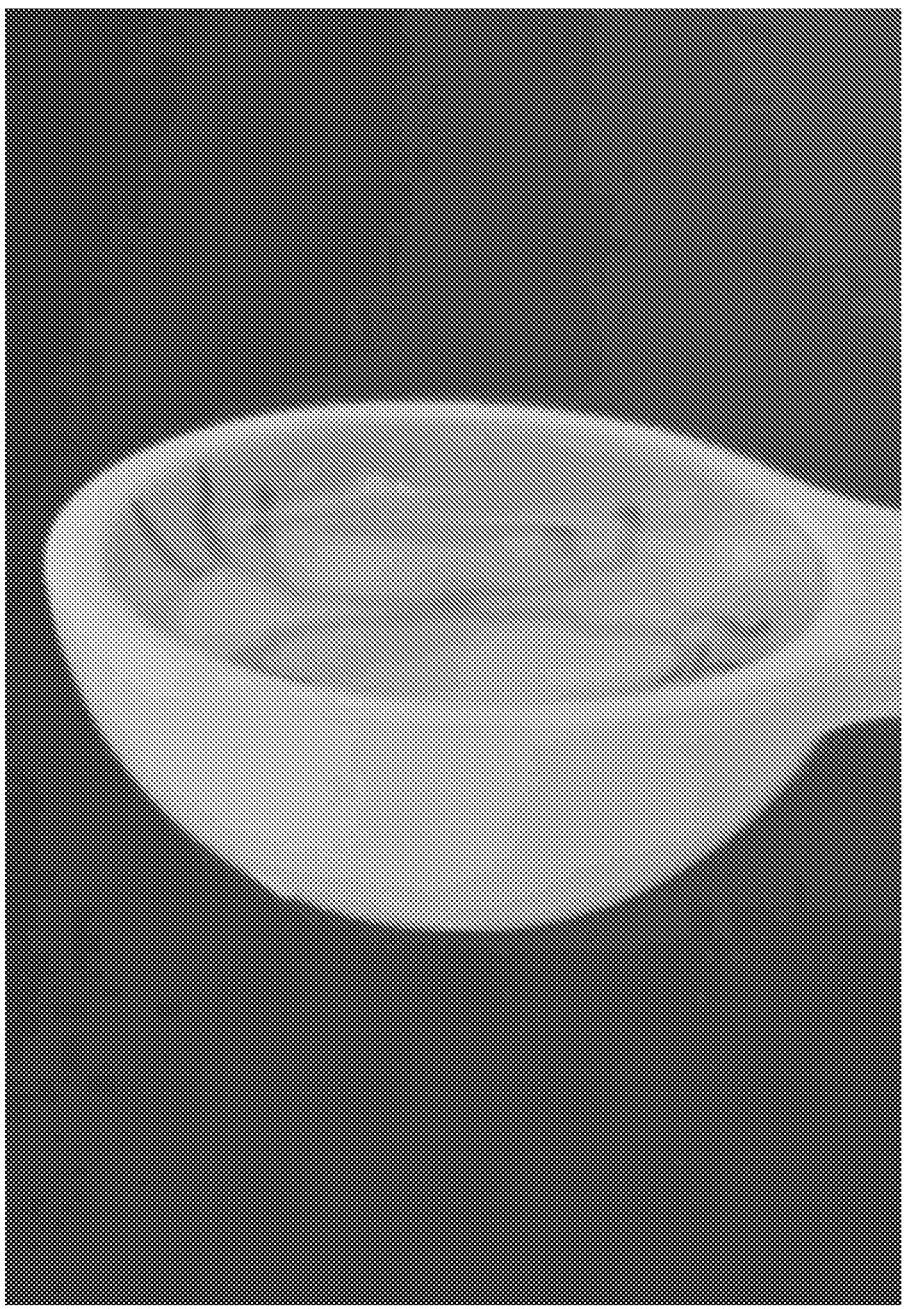
FIG. 6 is an illustration of a hydrogel that formed in a container, where the container is held in a vertical position, as further described in Example 5.

An aliquot of the TPVA solution from Example 2 was mixed with an equal volume of an aliquot of the PEGDA solution from Example 2 to produce a hydrogel premix. The premix was immediately loaded into a syringe having an injection needle with an inside diameter of approximately 300 micrometers. The premix was easily dispensed from the syringe through the injection needle. FIG. 5 is an illustration of hydrogel premix that has been dispensed from the syringe into a container. Once the hydrogel premix had been dispensed into the container, the hydrogel premix was observed to form a hydrogel in approximately 3-5 minutes at a temperature of approximately 37° C. FIG. 6 is an illustration of the hydrogel that formed in the container, where the container is held in a vertical position.

Example 6—In Vitro Toxicity Analysis for Exemplary Hydrogel

An aliquot of the TPVA solution described in Example 2 was mixed with an equal volume of an aliquot of a PEGDA solution described in Example 2 to produce a hydrogel premix contained in a 15 mL tube, noting that in this experiment (i) the thiolated poly(vinyl alcohol) was treated with ultra-violet light (254 nm) for a few minutes before mixing with phosphate buffered saline to form the TPVA solution, and (ii) the poly(ethylene glycol) diacrylate was treated with ultra-violet light (254 nm) for a few minutes before mixing with phosphate buffered saline to form the PEGDA solution. The hydrogel premix was allowed to gel for a duration of 20 minutes at a temperature of 37° C., in order to form the hydrogel.

Samples of the (i) thiolated poly(vinyl alcohol), (ii) poly (ethylene glycol) diacrylate, and (iii) hydrogel were subjected to in vitro toxicity analysis according to an ISO 10993-5 cytotoxicity protocol performed by Nelson Laboratories.

To test the in vitro toxicity of thiolated poly(vinyl alcohol), an aliquot of thiolated poly(vinyl alcohol) was mixed with serum-supplemented mammalian cell culture media (MEM) to generate a mixture that was 6% w/w thiolated poly(vinyl alcohol). The resulting mixture was applied to L929 cells. The cells were evaluated for evidence of toxicity effects due to the mixture. Results of the assay were that a score of 1 was observed indicating "slight cytotoxicity."

To test the in vitro toxicity of poly(ethylene glycol) diacrylate, an aliquot of poly(ethylene glycol) diacrylate was mixed with MEM to generate a mixture that was 3% w/w poly(ethylene glycol) diacrylate. The resulting mixture was applied to L929 cells. The cells were evaluated for evidence of toxicity effects due to the mixture. Results of the assay were that a score of 1 was observed indicating "slight cytotoxicity."

To test the in vitro toxicity of the hydrogel, the hydrogel was extracted with MEM, and the resulting extract was applied to L929 cells. The cells were evaluated for evidence of toxicity effects due to the extract. Results of the assay were that a score of 0 was observed indicating "no observed cytotoxicity."

Because a score of <2 is considered an acceptable level of cytotoxicity, all materials tested in this experiment were determined to have an acceptable level of cytotoxicity.

Example 7—In Vivo Toxicity Analysis for Exemplary Hydrogel

Figure 7:
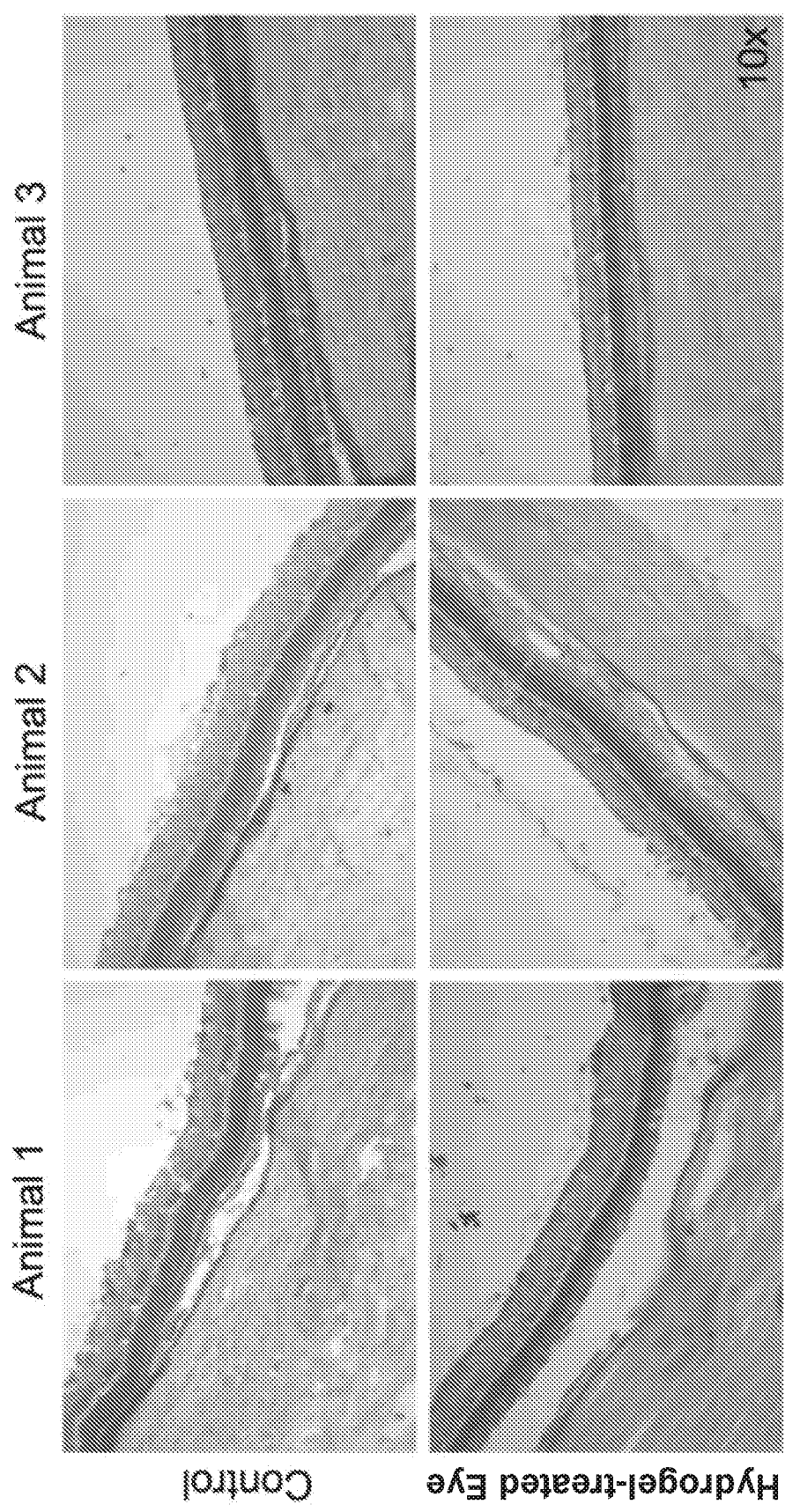
FIG. 7 is an illustration of histopathologic analysis of rabbit retinal tissue obtained on day 7 after intravitreal injection for rabbit eyes that (i) had received hydrogel premix ("hydrogel—treated eye") and (ii) had not received hydrogel premix (i.e., "control"), as further described in Example 7.

The left eye in each of three rabbits was subjected to intravitreal injection of the hydrogel premix from Example 2. The right eye in each of the three rabbits did not receive treatment and, therefore, was used as a "control." The rabbits' eyes were examined after intravitreal injection on the day of injection, and then again at 1, 2, 3, and 7 days after intravitreal injection. No evidence of inflammation, high intraocular-pressure in the eye, formation of cataracts, or retinal change was observed clinically. Additionally, histopathologic analysis of the rabbits' retinal tissue showed normal retinal architecture. FIG. 7 is an illustration of histopathologic analysis of rabbit retinal tissue obtained on day 7 after intravitreal injection for rabbit eyes that (i) had received hydrogel premix ("hydrogel-treated eye") and (ii) had not received hydrogel premix (i.e., "control").

Example 8—Use of Exemplary Hydrogel In Vitrectomy in Rabbit Eyes

Three rabbits were subjected to a 25 gauge pars plana vitrectomy to the left eye using hydrogel premix from Example 2. The procedure entailed peeling of the posterior hyaloid face, fluid air exchange, and then injecting the hydrogel premix into the eye of the rabbits. The rabbits were analyzed one week after completing the foregoing procedure. It was determined that all rabbits had normal intraocular pressure, had well-perfused optic nerves, and were healthy. Intraocular pressure values for the rabbits' eyes are presented in Table 2 below.

TABLE 2

| Subject Identification No. | Intra-ocular Pressure One Day After Injection of Hydrogel (mmHg) | | Intra-ocular Pressure Seven Days After Injection of Hydrogel (mmHg) | |
| --- | --- | --- | --- | --- |
| | Control Eye | Hydrogel-Treated Eye | Control Eye | Hydrogel-Treated Eye |
| 1 | 13 | 14 | 9 | 10 |
| 2 | 12 | 13 | 8 | 10 |
| 3 | 19 | 15 | 16 | 10 |

Figure 8:
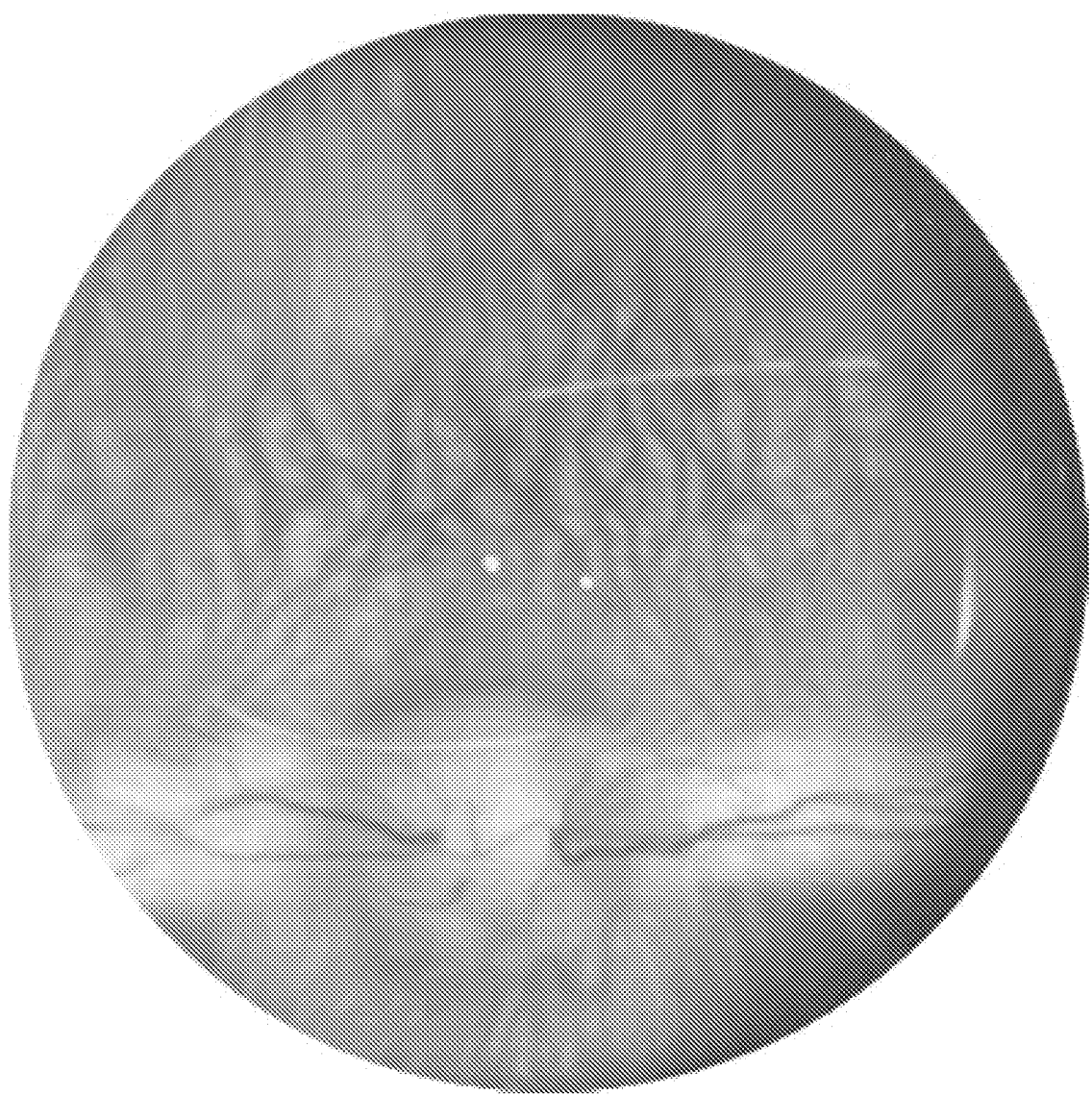
FIG. 8 is an illustration of a rabbit eye following a vitrectomy using the hydrogel according to procedures described in Example 8.

FIG. 8 provides an illustration of a rabbit eye 1 day after a vitrectomy was performed using the hydrogel according to this procedure. As depicted in FIG. 8, the rabbit eye was observed to have a normal appearance of the posterior pole.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of providing a retinal tamponade comprising a pharmaceutical composition in an eye of a subject, the method comprising:
   a. injecting an effective amount of a nucleo-functional polymer, an electro-functional polymer, and a pharmaceutical composition into the vitreous cavity of the eye of the subject; and
   b. allowing the nucleo-functional polymer and the electro-functional polymer to react to form a hydrogel, which forms the retinal tamponade comprising the pharmaceutical composition in the vitreous cavity;
       wherein the nucleo-functional polymer is a biocompatible polymer comprising poly(vinyl alcohol) containing a plurality of thio-functional groups —$R^1$—SH, wherein $R^1$ is an ester-containing linker, and the electro-functional polymer is a biocompatible polymer comprising poly(ethylene glycol) containing at least one thiol-reactive group.

2. The method of claim 1, wherein the retinal tamponade comprising the pharmaceutical composition is provided in the eye of a subject having a physical discontinuity in the retinal tissue, a tear in the retinal tissue, a break in the retinal tissue, or a hole in the retinal tissue.

3. The method of claim 1, wherein the retinal tamponade comprising the pharmaceutical composition is provided in the eye of a subject having undergone surgery for a macular hole, having undergone surgery to remove at least a portion of a epiretinal membrane, having undergone a vitrectomy for vitreomacular traction, having a rhegmatogenous retinal detachment, having tractional retinal detachment, or having serous retinal detachment.

4. The method of claim 1, wherein the nucleo-functional polymer and the electro-functional polymer are injected separately as liquid aqueous pharmaceutical compositions or together as a single, liquid aqueous pharmaceutical composition to the vitreous cavity of the eye of the subject.

5. The method of claim 4, wherein the separate liquid aqueous pharmaceutical compositions or single liquid aqueous pharmaceutical composition has a pH in the range of about 7.2 to about 7.6.

6. The method of claim 1, wherein the hydrogel has a refractive index in the range of from about 1.2 to about 1.5.

7. The method of claim 1, wherein the hydrogel has a transparency of at least 90% for light in the visible spectrum when measured through hydrogel having a thickness of 2 cm.

8. The method of claim 1, wherein the hydrogel has a gelation time of less than about 10 minutes.

9. The method of claim 1, wherein the hydrogel undergoes complete biodegradation from the eye of the subject within about 3 days to about 7 days, about 2 weeks to about 8 weeks, or about 4 months to about 6 months, or within 12 months or 24 months.

10. The method of claim 1, wherein the hydrogel has a biodegradation half-life in the range of from about 1 week to about 3 weeks or from about 8 weeks to about 15 weeks when disposed within the vitreous cavity of an eye.

11. The method of claim 1, wherein the hydrogel generates a pressure within the eye of less than 25 mmHg.

12. The method of claim 1, wherein the nucleo-functional polymer has a weight-average molecular weight in the range of from about 500 g/mol to about 1,000,000 g/mol; and
    wherein the electro-functional polymer has a weight-average molecular weight in the range of from about 500 g/mol to about 1,000,000 g/mol.

13. The method of claim 1, wherein the mole ratio of (i) thio-functional groups —$R^1$—SH to (ii) the at least one thiol-reactive group is in the range of 10:1 to 1:10, 5:1 to 1:1, or 2:1 to 1:1.

14. The method of claim 1, wherein the retinal tamponade comprising the pharmaceutical composition is provided in the eye of a subject having undergone a vitrectomy.

15. The method of claim 1, wherein $R^1$—SH is —OC(O)—($C_1$-$C_6$ alkylene)-SH.

16. The method of claim 1, wherein the poly(ethylene glycol) is linear, branched, a dendrimer, or multi-armed.

* * * * *